(12) United States Patent
Hambrock et al.

(10) Patent No.: US 10,188,230 B2
(45) Date of Patent: Jan. 29, 2019

(54) WIRELESS DRINK CONTAINER FOR MONITORING HYDRATION

(71) Applicant: Hidrate, Inc., Alexandria, MN (US)

(72) Inventors: Alexander Hambrock, Chicago, IL (US); Coleman Iverson, Minneapolis, MN (US); Ngoc Thi Van Nguyen, Chicago, IL (US); Alexandra Feeken, Alexandria, MN (US); Travis Heaver, Minneapolis, MN (US); Matt Engeriser, Eden Prairie, MN (US); Paul Schmokel, Eden Prairie, MN (US); Matthew Lewis, Alexandria, MN (US); Marc Cuva, Alexandria, MN (US); Nick Padilla, Alexandria, MN (US)

(*) Notice: Subject to any disclaimer, the term of this patent is extended or adjusted under 35 U.S.C. 154(b) by 0 days.

(21) Appl. No.: 15/488,033

(22) Filed: Apr. 14, 2017

(65) Prior Publication Data

US 2017/0340147 A1    Nov. 30, 2017

Related U.S. Application Data

(63) Continuation of application No. PCT/US2016/021482, filed on Mar. 9, 2016.
(Continued)

(51) Int. Cl.
*G01F 23/284* (2006.01)
*A47G 19/22* (2006.01)
(Continued)

(52) U.S. Cl.
CPC ............ *A47G 19/2227* (2013.01); *A45F 3/16* (2013.01); *A47G 23/16* (2013.01); *G01F 1/075* (2013.01);
(Continued)

(58) Field of Classification Search
CPC ............ A47G 19/2227; A47G 2200/18; A47G 2019/2244; A61J 2200/76; A61J 7/0481; G01F 23/00; G01F 23/2845
See application file for complete search history.

(56) References Cited

U.S. PATENT DOCUMENTS

| | | | | |
|---|---|---|---|---|
| 2,593,868 A | * | 4/1952 | Fowler | A47G 23/0216 116/324 |
| 3,996,879 A | * | 12/1976 | Walton | A61J 7/04 116/308 |

(Continued)

FOREIGN PATENT DOCUMENTS

| | | | | |
|---|---|---|---|---|
| DE | 10136236 A1 | * | 2/2003 | ............. A47G 23/16 |
| DE | 10138063 A1 | * | 2/2003 | ......... A47G 19/2227 |

(Continued)

OTHER PUBLICATIONS

Machine translation of JP-H-10281852 A which originally published on Oct. 1998.*
(Continued)

*Primary Examiner* — David A Rogers
(74) *Attorney, Agent, or Firm* — Cooley LLP

(57) ABSTRACT

A wireless drink container can monitor a person's hydration and prompt him or her to drink more if appropriate. The drink containers as described herein can monitor liquid levels and communicate with external devices about the liquid levels and rate of consumption. One or more sensors in the drink container monitor the liquid level within the container. A processor coupled to the sensor(s) estimates how much liquid has been removed from the container from changes in the liquid level and transmits a signal representing the change in liquid level to a smartphone or other external device. It also triggers an audio or visual indicator, such as an LED, that prompts the user to drink more based on the user's estimated liquid consumption and on the user's (Continued)

liquid consumption goals, which may be based on the user's physiology, activity level, and location.

28 Claims, 19 Drawing Sheets

Related U.S. Application Data

(60) Provisional application No. 62/210,723, filed on Aug. 27, 2015, provisional application No. 62/130,324, filed on Mar. 9, 2015.

(51) Int. Cl.
    *A47G 23/16*      (2006.01)
    *A45F 3/16*      (2006.01)
    *G01F 23/74*      (2006.01)
    *G01F 25/00*      (2006.01)
    *G01F 1/075*      (2006.01)
    *G01F 23/00*      (2006.01)
    *G01F 23/26*      (2006.01)
    *G01F 23/292*      (2006.01)
    *G01F 23/296*      (2006.01)

(52) U.S. Cl.
CPC ........ *G01F 23/0076* (2013.01); *G01F 23/263* (2013.01); *G01F 23/265* (2013.01); *G01F 23/296* (2013.01); *G01F 23/2921* (2013.01); *G01F 23/74* (2013.01); *G01F 25/0061* (2013.01); *A47G 2019/2238* (2013.01); *G01F 23/00* (2013.01); *G01F 23/2845* (2013.01)

(56) References Cited

U.S. PATENT DOCUMENTS

| | | | | |
|---|---|---|---|---|
| 4,450,722 A * | 5/1984 | Keyes, IV | .......... | G01F 23/2921 250/577 |
| 4,860,684 A * | 8/1989 | Al-Harbi | .......... | A61J 7/04 116/308 |
| 4,877,119 A * | 10/1989 | Hosking | .......... | A47G 23/16 116/227 |
| 4,904,878 A * | 2/1990 | Gipp | .......... | G01F 23/2921 250/577 |
| D314,689 S * | 2/1991 | Claudias | .......... | D10/2 |
| D333,066 S * | 2/1993 | Kimpson | .......... | D7/509 |
| 5,184,510 A * | 2/1993 | Rossman | .......... | G01F 23/0076 73/1.73 |
| D350,457 S * | 9/1994 | Bailey | .......... | D7/509 |
| 5,356,012 A * | 10/1994 | Tang | .......... | A61J 7/04 116/308 |
| 5,400,907 A * | 3/1995 | Chen | .......... | A47G 19/2227 206/459.1 |
| 5,492,246 A * | 2/1996 | Bailey | .......... | A47G 23/14 116/315 |
| 5,607,078 A * | 3/1997 | Nordberg | .......... | A47G 23/16 116/227 |
| 5,644,298 A * | 7/1997 | Brooks | .......... | A47G 23/16 206/534 |
| 5,789,675 A * | 8/1998 | Blaine | .......... | G01F 23/284 340/612 |
| 5,808,200 A * | 9/1998 | Dam | .......... | G01N 29/024 73/610 |
| 5,845,777 A * | 12/1998 | Najmi | .......... | A47G 23/16 116/227 |
| 5,860,387 A * | 1/1999 | Giveen | .......... | A61J 9/0008 116/285 |
| D404,969 S * | 2/1999 | Krenzler | .......... | D7/507 |
| 5,881,597 A * | 3/1999 | Brooks | .......... | G01F 19/00 73/428 |
| 5,896,990 A * | 4/1999 | Barzana | .......... | A61J 7/04 116/309 |
| 5,979,698 A * | 11/1999 | Deal | .......... | A61J 7/04 116/205 |
| 6,163,248 A | 12/2000 | Peek et al. | | |
| 6,206,229 B1 * | 3/2001 | Harjes | .......... | B65D 1/265 220/669 |
| 6,212,803 B1 * | 4/2001 | Key | .......... | B65C 3/065 215/252 |
| 6,212,959 B1 | 4/2001 | Perkins | | |
| 6,252,494 B1 * | 6/2001 | Howell | .......... | A47G 23/16 340/309.3 |
| D477,500 S * | 7/2003 | Smith | .......... | D7/515 |
| 6,588,593 B2 * | 7/2003 | Woskoski | .......... | A47G 19/2227 206/217 |
| D489,571 S * | 5/2004 | Lee | .......... | D7/507 |
| 6,793,075 B1 * | 9/2004 | Jeter | .......... | A47G 19/2272 206/459.1 |
| 6,943,566 B2 * | 9/2005 | Florin | .......... | G01F 23/266 324/662 |
| 6,990,860 B1 * | 1/2006 | Gillanders | .......... | A45F 3/20 222/175 |
| 7,004,105 B2 * | 2/2006 | Bucksch | .......... | A47G 23/16 116/227 |
| 7,344,508 B2 | 3/2008 | Surina | | |
| 7,493,232 B1 | 2/2009 | Surina | | |
| 7,581,640 B2 * | 9/2009 | Lopez | .......... | A47G 23/16 206/459.1 |
| 7,600,423 B1 * | 10/2009 | Fluhler | .......... | G01F 23/26 73/290 B |
| 7,712,364 B2 * | 5/2010 | Radhakrishnan | ....... | A47J 31/50 73/304 C |
| 7,851,775 B2 * | 12/2010 | Hoyt | .......... | G01F 3/10 250/231.15 |
| 8,072,594 B1 * | 12/2011 | McMahon | .......... | G01F 23/2927 250/577 |
| 8,378,830 B2 | 2/2013 | Moran | | |
| 8,446,283 B2 * | 5/2013 | Pietrorazio | .......... | G01F 23/292 340/580 |
| 8,550,269 B2 | 10/2013 | Lane | | |
| 8,689,989 B2 | 4/2014 | Lane | | |
| 8,907,796 B2 * | 12/2014 | Sweeney | .......... | A47G 19/2272 220/203.23 |
| 8,979,539 B1 * | 3/2015 | Snyder | .......... | G09B 19/0092 128/921 |
| 9,151,605 B1 | 10/2015 | Sweeney et al. | | |
| 9,230,423 B2 * | 1/2016 | Wu | .......... | G08B 21/24 |
| 9,311,806 B2 * | 4/2016 | Hazen | .......... | G08B 21/182 |
| 9,320,375 B2 | 4/2016 | Sweeney et al. | | |
| 9,327,960 B2 | 5/2016 | Sweeney et al. | | |
| 9,382,107 B2 | 5/2016 | Von Hollen | | |
| 9,380,897 B2 | 7/2016 | Pfeiffer | | |
| D769,063 S | 10/2016 | Sweeney | | |
| 9,792,409 B2 * | 10/2017 | Wernow | .......... | G06F 19/3418 |
| 2001/0015099 A1 * | 8/2001 | Blaine | .......... | G01F 23/284 73/290 R |
| 2002/0129663 A1 * | 9/2002 | Hoyt | .......... | G01F 1/115 73/861.79 |
| 2005/0099304 A1 * | 5/2005 | Humphrey | .......... | G06Q 20/105 340/572.8 |
| 2005/0284219 A1 * | 12/2005 | Kalix | .......... | G01F 23/02 73/293 |
| 2006/0000277 A1 * | 1/2006 | Pietrorazio | .......... | G01F 22/00 73/293 |
| 2006/0132351 A1 * | 6/2006 | Le Sesne | .......... | G01F 23/284 342/124 |
| 2007/0068249 A1 * | 3/2007 | Eguchi | .......... | B41J 2/14427 73/304 R |
| 2009/0122523 A1 * | 5/2009 | Rycroft | .......... | A47G 19/2227 362/101 |
| 2010/0000317 A1 * | 1/2010 | Bron | .......... | A47J 27/2105 73/313 |
| 2010/0001022 A1 | 1/2010 | McInerney | | |
| 2010/0163567 A1 * | 7/2010 | Chiang | .......... | A47G 23/16 220/703 |
| 2011/0149693 A1 * | 6/2011 | Liao | .......... | G04C 23/48 368/10 |
| 2011/0265562 A1 * | 11/2011 | Li | .......... | A47J 27/212 73/304 C |

(56) References Cited

U.S. PATENT DOCUMENTS

| | | | |
|---|---|---|---|
| 2012/0094261 A1 | 4/2012 | Hayn et al. | |
| 2012/0097567 A1* | 4/2012 | Zhao | A47G 23/16 |
| | | | 206/459.1 |
| 2012/0103926 A1* | 5/2012 | Ibsies | B65B 3/04 |
| | | | 215/228 |
| 2012/0118059 A1* | 5/2012 | Reimer | F01N 3/2066 |
| | | | 73/290 V |
| 2013/0216877 A1* | 8/2013 | Campbell | H01M 10/484 |
| | | | 429/91 |
| 2013/0275075 A1* | 10/2013 | Johnson | G06M 1/00 |
| | | | 702/127 |
| 2013/0319915 A1 | 12/2013 | Gellibolian et al. | |
| 2014/0174173 A1* | 6/2014 | Chamberlin | G01F 23/24 |
| | | | 73/304 R |
| 2014/0303790 A1* | 10/2014 | Huang | G06Q 50/22 |
| | | | 700/281 |
| 2014/0311239 A1 | 10/2014 | Marjanovic et al. | |
| 2014/0341411 A1* | 11/2014 | Mohindra | H04R 1/021 |
| | | | 381/334 |
| 2014/0354438 A1 | 12/2014 | Hazen et al. | |
| 2014/0372045 A1 | 12/2014 | Keski-Pukkila et al. | |
| 2015/0108026 A1* | 4/2015 | Azimi | G06F 19/3475 |
| | | | 206/459.1 |
| 2015/0122688 A1* | 5/2015 | Dias | A47G 19/025 |
| | | | 206/459.1 |
| 2015/0182797 A1 | 7/2015 | Wernow et al. | |
| 2016/0022209 A1* | 1/2016 | Fraisl | A45F 3/16 |
| | | | 600/590 |
| 2016/0025545 A1* | 1/2016 | Saltzgiver | G01F 23/263 |
| | | | 73/304 C |
| 2016/0220184 A1* | 8/2016 | Manion | A61B 5/4875 |
| 2016/0286993 A1* | 10/2016 | Pau | A47G 23/16 |
| 2017/0273488 A1* | 9/2017 | Lonis | A47G 19/2227 |

FOREIGN PATENT DOCUMENTS

| | | | |
|---|---|---|---|
| EP | 0989989 A1 * | 2/2000 | |
| FR | 2323130 A * | 5/1997 | |
| JP | 10281852 A * | 10/1998 | |
| NL | 1 039 558 C | 10/2013 | |
| WO | WO 2011/004319 A1 | 1/2011 | |
| WO | WO 2013/181455 A1 | 12/2013 | |

OTHER PUBLICATIONS

U.S. Appl. No. 62/018,079, filed Jun. 27, 2014.*
U.S. Appl. No. 62/162,510, filed May 15, 2015.*
Hidrate Pitch Presentation PowerPoint slides, Sep. 14, 2014, 6 pages.
"Hi! It's time to drink more water," Hidrate Pitch Presentation PowerPoint Slides, Sep. 14, 2014, 15 pages.
TECHdotMN, Startup Weekend Twin Cities 6 final pitches, Sep. 16, 2014. Retreived from https://tech.mn/news/2014/09/16/startup-weekend-twin-cities-6-final-pitches/, 11 pages.
International Search Report and Written Opinion dated Jun. 6, 2016 for International Application No. PCT/US2016/021482, 11 pages.
Communication Pursuant to Article 94(3) dated Sep. 20, 2018 for European Application No. 16716327.8, 6 pages.

* cited by examiner

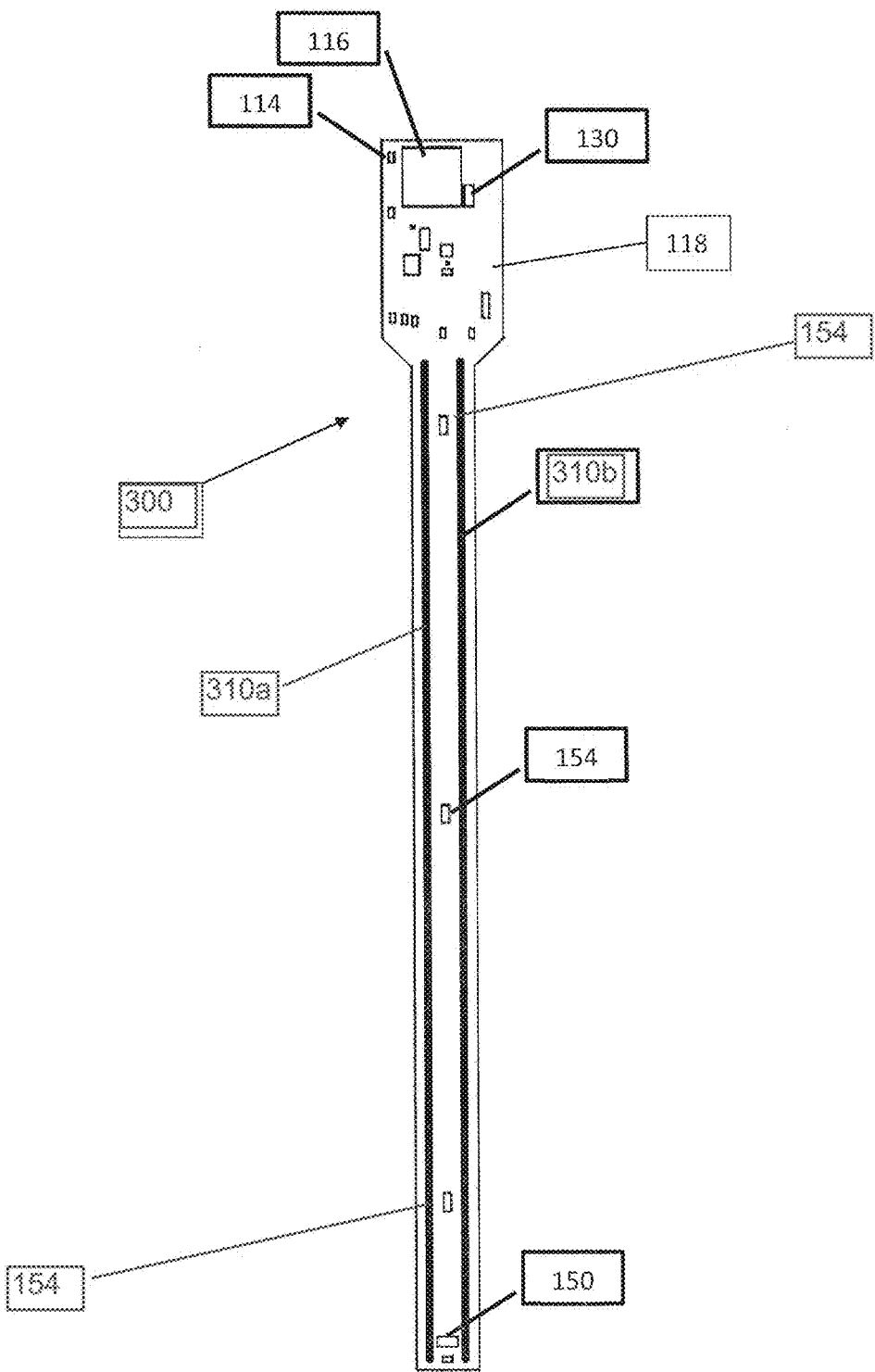

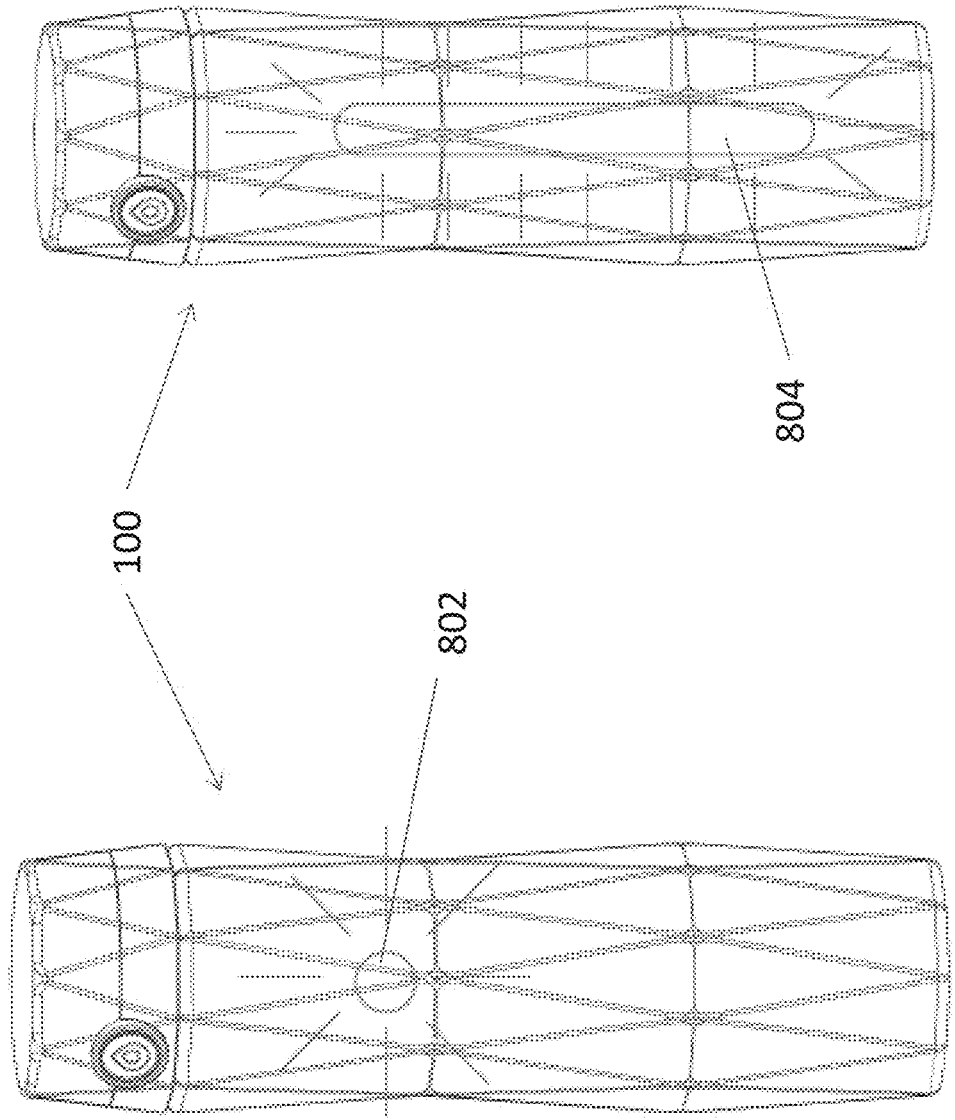

WIRELESS DRINK CONTAINER FOR MONITORING HYDRATION

CROSS-REFERENCE TO RELATED APPLICATIONS

This application is a bypass continuation of International Application No. PCT/US2016/021482, filed Mar. 9, 2016, and titled "Wireless Drink Container for Monitoring Hydration," which in turn claims the priority benefit, under 35 U.S.C. § 119(e), of U.S. Application No. 62/210,723, filed Aug. 27, 2015, and titled "Wireless Drink Container for Monitoring Hydration," and from U.S. Application No. 62/130,324, filed Mar. 9, 2015, and titled "Wireless Drink Container for Monitoring Hydration," the entire contents of each of which is incorporated herein by reference.

BACKGROUND

Wearable devices, such as smartwatches and fitness bracelets are some of the new examples of connected devices that can monitor the wearer's physical activities during the day or while asleep. These are developed to personify or individualize help by specifically tailoring for the wearer (or user) by tracking the wearer's health and well-being. In another word, these modern devices enable individualized monitoring, which can be further augmented or supported by tethering to an external portable computing device for various ancillary computation and/or communication capabilities.

While these smart devices can track the wearer's physical activities to better inform the wearer of his or her activity levels, there are still not many devices that can inform the wearer on other important aspects, for example, nutrition intake or hydration levels. Proper hydration is essential, but some studies show that over 90% of people have poor water consumption habits and fewer than 5% regularly consume enough water. Encouraging proper hydration can improve health and quality of life.

SUMMARY

The present disclosure relates generally to portable drink containers that monitor liquid levels and communicate with software applications on external devices about the liquid levels and rate of liquid consumption. One embodiment of this technology is a container assembly that includes a container defining a cavity, a liquid level sensor disposed in the cavity, a processor operably coupled to the liquid level sensor, and a visual indicator operably coupled to the processor and disposed within the cavity. The cavity holds a liquid, and the liquid level sensor measures a level of the liquid in the cavity. The processor polls the liquid level sensor for a measurement of the level of the liquid in the cavity and estimates a change in the level of the liquid in the cavity based on the measurement of the level of the liquid in the cavity. And the visual indicator provide a visual indication prompting a user to drink from the container.

Examples of the container assembly may also include an accelerometer that is mechanically coupled to the container and operably coupled to the processor. The accelerometer intermittently measures an acceleration of the container. The processor may poll the accelerometer intermittently and poll the liquid level sensor if data from the accelerometer indicates that the container is vertically oriented. The processor may also estimate the change in the level of the liquid in the cavity based on data from the accelerometer.

The container assembly may also include an antenna that is operably coupled to the processor. In operation, the antenna transmits an indication of the change in the level of the liquid in the cavity to a wireless device, such as a cell phone. The processor may be configured to cause the visual indicator to provide the visual indication in response to a command received from the wireless device via the antenna. This command may be based at least in part on a time since the visual indicator provided the a last or most recent visual indication. The antenna may receive an indication of a target change in the level of the liquid in the cavity from the wireless device. And the processor may compare the change in the level of the liquid in the cavity to the target change in the level of the liquid in the cavity and cause the visual indicator to provide the visual indication if the change in the level of the liquid in the cavity is less than the target change in the level of the liquid in the cavity. This target change in the level of the liquid in the cavity can be based on an age of a user, a height of the user, a weight of the user, an activity level of the user, a location of the user, an ambient temperature, and/or an ambient humidity.

The visual indicator may include one or more light-emitting diodes (LEDs) disposed along a substrate extending into the cavity. The LEDs may provide the visual indication by emitting light on a periodic basis.

The container assembly can include a cap and a cap sensor operably coupled to the processor. The cap keeps the liquid within the cavity, and the cap sensor senses if the cap is coupled to the container. The processor polls the liquid level sensor if the cap sensor indicates that the cap is coupled to the container.

Another embodiment of the present technology includes a method of tracking consumption, by a user, of a liquid disposed within a container. This method comprises measuring, with an accelerometer mechanically coupled to the container, an acceleration of the container. A processor operably coupled to the accelerometer estimates an orientation of the container based on the acceleration of the container and determines if the orientation is within a predefined range of orientations (e.g., if the container is approximately vertically oriented). If the orientation is with the predefined range of orientations, a liquid level sensor operably coupled to the processor measures a level of the liquid in the container. The processor estimates a change in the level of the liquid in the cavity based on the level of the liquid in the cavity measured by the liquid level sensor and, optionally, the orientation of the container. These steps may be repeated, e.g., at periodic intervals, predetermined intervals, on command, etc.

The method may also include sensing, with a cap sensor operably coupled to the processor, if a cap is coupled to the container. The liquid level sensor may measure the level of the liquid (only) if the cap sensor indicates that the cap is coupled to the container.

The method may further include transmitting, via an antenna operably coupled to the processor, an indication of the change in the level of the liquid in the container to a wireless device. The antenna may also receive an indication of a target change in the level of the liquid from the wireless device. This target change in the level of the liquid in the cavity can be based on an age of a user, a height of the user, a weight of the user, an activity level of the user, a location of the user, an ambient temperature, and/or an ambient humidity. In these cases, the processor may compare the change in the level of the liquid in the cavity to the target change in the level of the liquid.

If the change in the level of the liquid is less than the target change in the level of the liquid, the processor may cause a light source disposed in or on the container to provide a visual indication to the user.

The processor may also cause the light source to emit light in order to prompt the user to drink the liquid in the container. The light source may emit the light at periodic intervals (e.g., every two hours). The light source may also emit light in response to a command from a wireless device. This command may be based on (1) a comparison of the change in the liquid level to a target change in the level of the liquid and/or (2) a time since the last time the light source emitted light.

Additional embodiments of the present technology include a container assembly that comprises a translucent container, a substrate, a liquid level sensor disposed on the substrate, an accelerometer mechanically coupled to the translucent container, a processor operably coupled to the accelerometer and the liquid level sensor, an antenna operably coupled to the processor, and a light source disposed on the substrate and operably coupled to the processor. The translucent container holds a liquid. The substrate extends at least partway into the liquid. The liquid level sensor measures a level of the liquid. The accelerometer measures an acceleration of the translucent container. The processor periodically determines an orientation of the translucent container based on acceleration measured by the accelerometer. The processor also periodically determines a change in the level of the liquid in the cavity based on the level of the liquid measured by the liquid level sensor and the orientation of the translucent container. The antenna transmits the change in the level of the liquid to a wireless device. And the light source emits light at periodic intervals and/or in response to a command received from the wireless device via the antenna. This command may be based on (i) a comparison of the change in the level of the liquid and a desired change in the level of the liquid and (ii) a time since a last emission of light from the light source.

In another example, a portable drink container features an electronic system that transmits data regarding the change of the liquid quantity within the container to an external device, such as a smartphone or tablet. A sensor in the container monitors the level of liquid within the container and compares relative changes in the liquid level to estimate how much liquid has been removed from the container. In another embodiment, when a user drinks from the container, a flow sensor in the container's lid tracks the volume of fluid exiting the container and transmits a signal representing the fluid flow to an external device. In both cases, relevant information from the drink container is transmitted as data to an external software application which calculates liquid consumption goals based on the user's physiology, activity level, and location.

In some embodiments of the present disclosure, apparatus and systems for monitoring a person's fluid intake are presented. For example, a fluid container assembly capable of communicating with an external server is disclosed. In some embodiments, the fluid container assembly is configured to monitor and/or assess features related to fluids contained in the container so as to determine the fluid intake of the user of the container assembly. Examples of such features include amount of the fluid (e.g., absolute amount and/or changes in the fluid level), type of fluid, temperature, pH level, contents (e.g., constituent elements of the fluid), contaminants, and/or the like. The container assembly may comprise components capable of gathering data on such features. For example, the container assembly may contain sensors such as an electrode level sensor, a float sensor, etc., for determining the fluid level in the container. As another example, the container assembly may contain one or more sensors, such as a liquid content sensor, a temperature sensor, a clock, a pH sensor, etc., for determining the type and/or properties of the fluid in the container. In some embodiments, the container assembly may comprise a positional detector for measuring the container assembly's position and/or orientation, examples of which include a gyroscope, an accelerometer, and combination thereof. For example, an accelerometer can be used to measure the orientation (e.g., tilt) of the container assembly. The data gathered from the various components of the container assembly (e.g., electrode level sensor, float sensor, liquid content sensor, temperature sensor, pH sensor, clocks, position detector, etc.) can in turn be used to determine the fluid level in the container.

In some embodiments, the container assembly may comprise the processing capability to evaluate the gathered data to estimate or determine the user's fluid intake. In some embodiments, the container assembly may comprise a processor onboard for processing the gathered data. For example, based on the changes in the level of fluid in the fluid container, the processor may determine the amount of fluid consumed by the user. In some embodiments, the container assembly may comprise a communications component (e.g., transceiver) for communicating with external servers. For example, the communications component may transmit the gathered data to an external server that performs some or all of the evaluation to determine the user's fluid intake. In some embodiments, the communications component may be capable of receiving signals from external servers. For example, the communications component may receive the results of the evaluation of the transmitted data, and/or it may receive signals comprising server-initiated instructions based on the determination of the user's fluid intake (e.g., instructions commanding the processor to send a notification to the user to consume additional amount of fluid).

A user interface included in the container assembly can be configured to present information by displaying and/or broadcasting notifications from the onboard processor and/or an external server. The notifications can be in the form of texts, visual (e.g., lights from light emitting diode (LED) light sources, etc.), video, audio, and/or the like. In some embodiments, the user interface may also be configured to receive a user input in any of the aforementioned forms and/or via one or more buttons, touch screens, etc.

In some embodiments, the fluid container assembly may include a container that defines a cavity or capsule for receiving fluids, and a lid (removable or otherwise) for covering an opening of the cavity of the container. In some embodiments, the container may be designed to be "insulated glazed," i.e., two or more container walls may be separated by a vacuum or a medium capable of providing desired insulation. Further, the container may be constructed to handle a wide array of adverse conditions, including extreme heat or cold, pressure, contact with hostile environments, and the like. The outer surface of the container may be textured, coated, etc., to provide a more secure grip. In some embodiments, the container and the lid may be affixed by any number of fastening methods, including threading, screws, nuts and bolts, glue, snap-fittings, welding or the like.

In some embodiments, the lid may provide housing for some or all electronics components of the fluid container assembly. For example, the lid may contain partially or completely one or more of the sensors, processor, user interface and/or display, communications component, memory for storing data, power source, and/or the like. In some embodiments, any of these electronic elements may be housed in other parts of the fluid container assembly, such as but not limited to the base container, a handle, an attachment, etc.

In some embodiments, one or more of the sensors may comprise sensors configured to monitor the state of the fluid container assembly and/or the liquid contained within the container. For example, one of the sensors may be a fluid level sensor configured to determine the level of fluid at the moment of measurement. A transceiver coupled to the sensor(s) may transmit data to a smartphone, server, or other processor-device for analysis.

In some embodiments, the processor and/or an external server may compare a measured level of fluid to a baseline level to calculate the change in the amount of fluid so as to deduce the fluid intake by the user of the fluid container assembly. The baseline level can be an initial measurement of fluid level taken by the fluid level sensor, and/or an amount entered into the user interface (for example, by the user) and/or the server indicating the fluid level prior to the start of fluid container assembly use by the user. In some embodiments, the fluid level sensor may perform successive measurements over time to deduce the amount and/or rate of change of the fluid level in the container. Based on such measurements, the amount and/or rate of fluid intake of the user may be determined. For example, the user's fluid intake may be substantially the same as the change in the fluid level of the container, or the fluid intake may not necessarily be substantially the same but related to the change in the fluid level (e.g., the fluid intake may be offset by a certain amount from the change in the fluid level due to spillage, errors in sensor calibration, measurements, etc.).

In some embodiments, the fluid level sensor may take the form of a capacitive structure connected to the lid and extending substantially perpendicular to the plane of the lid. The capacitive structure comprises at least two electrodes shaped and sized so that the capacitive structure can fit within the cavity of the base container. Consequently, when the lid is mounted on the fluid container assembly, the capacitive structure may extend at least a substantial portion of the length of the fluid container assembly within the cavity of the base container. For example, the connection of the capacitive structure to the lid may be configured so as to allow the capacitive structure to run substantially parallel to the length of the base container along any axis (e.g., through the centroid of the base container) when the lid is mounted on the base container. In some embodiments, the capacitive structure may be shielded from the fluid contained within the base container by liquid impermeable barrier or coating made from materials such as plastic, polymer, etc.

In some embodiments, the capacitive structure may comprise a parallel plate capacitor, i.e., substantially parallel electrodes spaced apart some distance from each other. In some instances, the capacitor may comprise more than two plates. In some embodiments, the capacitive structure may comprise a plurality of capacitors spaced apart along the length of at least a pair of electrodes. In any case, the capacitance as measured by a capacitive structure inserted inside a cavity containing a fluid may change as the fluid level varies within the base container. For example, as a user of the fluid container assembly consumes the fluid inside the base container, the level of the fluid changes, changing the capacitance(s) measured by the capacitive structure. For instance, as the fluid level changes from a baseline level (e.g., full fluid level) to less than full (e.g., half), the capacitance may also change, and from the change in the capacitance, a processing unit such as a processor onboard the fluid container assembly or in an external device, such as a smartphone or server, may deduce the change in the fluid level. This change is taken to represent roughly the amount of fluid consumed by the user of the fluid container assembly.

In some embodiments, the capacitance measurement may be taken regularly (e.g., periodically, continuously, etc.), allowing the processing unit to also determine the rate of change of the fluid level, i.e., roughly rate of fluid intake by the user from the fluid container assembly. In such embodiments, time measurements from the clock contained in the fluid container assembly may be used to determine the rate of fluid level change within the container. Further, measurements from other sensors may be used in adjusting the determined fluid level change and/or rate of change. For example, the processing unit may incorporate and adjust for orientation measurements (e.g., tilt of the container) from the accelerometer in determining fluid levels.

In some embodiments, the fluid level sensor can take the form of a marker rod and float structure wherein the rod may be connected to the lid and extend substantially perpendicular to the plane of the lid. The rod may be shaped and sized so as to fit within the cavity of the base container, i.e., when the lid is mounted on the fluid container assembly, the marker rod may extend at least a substantial portion of the length of the fluid container assembly within the cavity of the base container. For example, the connection of the marker rod to the lid may be configured so as to allow the marker rod to run substantially parallel to the length of the base container along any axis (e.g., through the centroid of the base container) when the lid is mounted on the base container. In some embodiments, the marker rod may be shielded from the fluid contained within the base container by liquid impermeable barrier or coating made from materials such as plastic, polymer, etc.

In some embodiments, the marker rod and float structure may be configured to establish the location of the float within the base container. For example, the marker rod and float structure may comprise a proximity sensor wherein the marker rod monitors the location of the float as the fluid level changes, thereby changing the location of the float. Examples of such proximity sensors include optical sensors, magnetic sensors, capacitive sensors, sonar sensors (e.g., ultrasonic sensors, etc.), electromagnetic sensors including infrared (IR) sensors, radio-frequency identification (RFID) sensor, etc., inductive sensors, Hall Effect sensors, and combinations thereof.

In some embodiments, the marker rod may comprise a Hall Effect sensor while the float comprises a magnetic element. When the fluid level varies within the base container, the relative location of the float with respect to the marker rod may also change. The magnetic field emitted by the float and received by the Hall Effect sensor changes as well, allowing the Hall Effect sensor to track the motion and/or location of the float. In some embodiments, the float location can be correlated with fluid level, and changes in the float location and motion of the float can be used to determine a user's fluid intake amount and/or rate.

For example, as a user of the fluid container assembly consumes the fluid inside the base container, the level of the fluid changes, changing the location of the float registered at the marker rod. In some embodiments, the marker rod may comprise a plurality of Hall Effect sensors spaced apart along the length of the marker rod. As the fluid level changes from a baseline level (e.g., full fluid level) to less than full (e.g., half full), the location of the float changes, triggering one or more of the Hall Effect sensors along the marker rod that are in the vicinity of the float. Accordingly, the location of the float within the base container as detected by Hall Effect sensors on the marker rod may be processed by a processing unit such as a processor onboard the fluid container assembly and/or an external server to deduce the change in the fluid level, i.e., roughly the amount of fluid consumed by the user of the fluid container assembly.

The rate of change of fluid level (e.g., rate of fluid consumption) may also be determined by the processing unit by utilizing temporal measurements by clocks in the fluid container assembly, etc. For example, if more than one Hall Effect sensor registers the position of the float, a weighted average of the measurements may be selected as the location of the float. Further, measurements from other sensors may be used in adjusting the determined fluid level change and/or rate of change. For example, the processing unit may incorporate and adjust for orientation measurements (e.g., tilt of the container) from the accelerometer in determining the location of the float, and correspondingly, fluid levels.

In some embodiments, the float may comprise a Hall Effect sensor and the marker rod may comprise a plurality of spaced magnetic elements along the rod. Similar to the preceding description, a change in the fluid level may change the location of the float with respect to the rod, and one or more magnetic elements on the rod and in the vicinity of the float may trigger the Hall Effect sensor when the float is proximate to the magnetic elements. Using a baseline triggering event (e.g., first trigger corresponds to full fluid level), in some embodiments, changes in fluid level may be determined from Hall Effect sensor triggers that ensue as the fluid level changes and the float's location varies (without refilling of the container).

Similar to the example above with respect to Hall effect proximity sensors, in some embodiments, the aforementioned proximity sensors may comprise an emitter and a receiver type structure for identifying the location of the float within the base container, and thereby allow for determining changes in the fluid level in the base container. For example, the float may comprise electromagnetic sensors that emit or receive electromagnetic (EM) signals (e.g., IR, RF, microwave, etc.), and correspondingly, the marker rod may comprise sensors that respectively receive or emit the EM signals. As another example, the float may comprise optical or sonar sensors that emit to or receive from the marker rod characteristic waves (e.g., light for optical and sound for sonar, etc.) that allow the identification and/or tracking of the float's location within the base container, thereby facilitating the determination of fluid level change (in some embodiments, including the rate of change as well) inside the base container.

In some embodiments, drawing accurate conclusion regarding fluid consumption of a user from a determined change in fluid levels of the container may depend on whether the lid is mounted on the container. For example, the user may consume the fluid in the container through a spout on the lid when the lid is securely mounted onto the base container. As such, any fluid level measurements taken when the lid is not detected to be mounted on the base container may be discounted in calculating the user's fluid consumption.

To that effect, proximity sensors may be installed on the container and the fluid level sensor that detect the mounting, or lack thereof, of the lid onto the container. Similar to the operation of the proximity sensors with respect to the aforementioned marker rod and float structure of the fluid level sensor, in some embodiments, the proximity sensors may comprise an emitter and a receiver, with one of the emitter and the receiver located on the sensor and the other located on the base. For example, the proximity sensor may be a Hall effect proximity sensor, and the magnetic element may be located at the distal end of the fluid level sensor while the Hall effect sensor may be located on the container. Accordingly, when the lid is removed from the base container, the magnetic element may be beyond the range of the Hall effect proximity sensor, and the lack of indication from the sensor that the magnetic element is in the vicinity of the sensor may indicate to a processing unit that the fluid level measurements should not be used in calculating a user's fluid consumption. In some embodiments, the proximity sensor may register the presence of the emitter; however, based on a threshold of signal strength, the proximity sensor and/or the processing unit may determine that the lid is not adequately coupled to the base container, and as such the fluid level measurements should not be used in calculating a user's fluid consumption.

Other examples of proximity sensors comprise emitters and receivers of IR, RFID, ultrasonic signals, etc. In such embodiments, the lack of detection of the signals or the detection of signals below a threshold signal strength may be interpreted to indicate that the fluid container assembly is not mounted at least adequately on the base container and that measurements of fluid level should not be used in determining a user's fluid consumption.

In some embodiments, the fluid container assembly comprises a fluid flow sensing system for detecting the flow of fluid out of the container and determining its rate of flow. For example, the lid of the fluid container assembly may comprise a flow rate sensor that measures the rate of flow of fluid out of a spout located on the lid and transmit such measurement to a processing unit such as a processor onboard the fluid container assembly and/or an external server. For example, an impeller located in the lid and configured to rotate as fluid flows out of the spout may be used to measure the fluid flow rate, as the rotation speed of the impeller can be correlated with the fluid flow rate. In some embodiments, the correlation may be performed at the processing unit.

Other examples of fluid flow sensors or meters include fluid velocimeters that measure the speed of the fluid flowing through the spout, ultrasonic flow meters, infrared flow sensors, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 3 shows a capacitive liquid level sensor suitable for use with the smart water bottle shown in FIG. 1A and the cap shown in FIG. 2A.

FIGS. 8A-8F illustrate how one or more visual indicators (e.g., LEDs) can be used to create various "glowing" effects that may prompt the user to drink more.

DETAILED DESCRIPTION

Figure 1A:
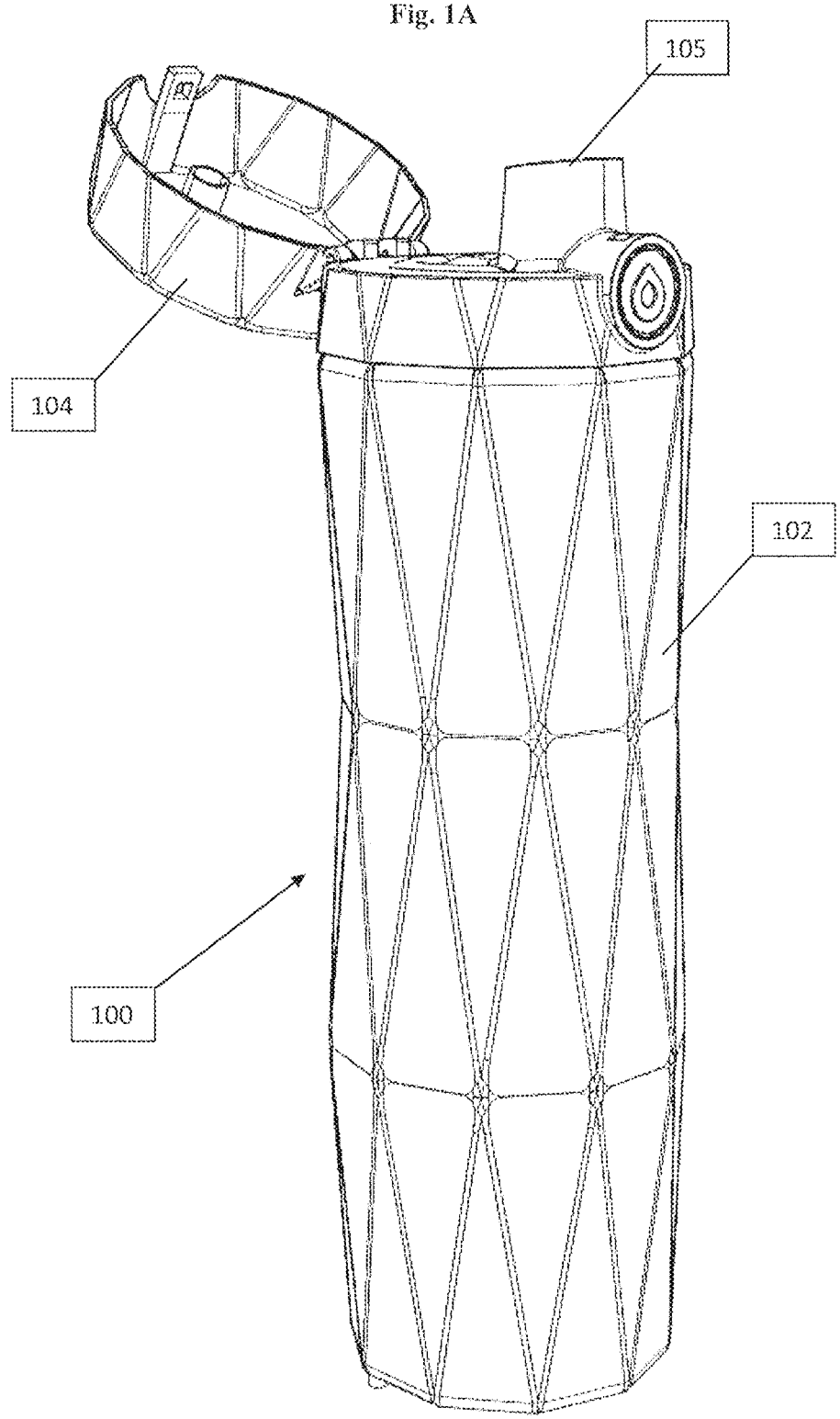
FIGS. 1A-1C show different views of a smart water bottle.

In the following detailed description, for purposes of explanation, numerous specific details are set forth in order to provide a thorough understanding of the various aspects of the presently disclosed subject matter. However, it will be evident to those skilled in the art that the presently disclosed subject matter may be practiced without these specific details. In other instances, well-known methods, procedures, and components have not been described in detail so as not to obscure the presently disclosed subject matter.

Various user interfaces and embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims. It is understood that various omissions and substitutions of equivalents are contemplated as circumstances may suggest or render expedient, but these are intended to cover application or embodiments without departing from the spirit or scope of the claims attached hereto. Also, it is to be understood that the phraseology and terminology used herein are for the purpose of description and should not be regarded as limiting.

The present disclosure describes embodiments of a wireless drink container, also called a smart water bottle, for monitoring hydration. In an embodiment, the smart water bottle includes a liquid container with a sensor that tracks the liquid quantities within the liquid container. The smart water bottle can also include a wireless transceiver, such as a Bluetooth transceiver, that transmits liquid level data from the liquid container to an external computing device, such as a smartphone. In some cases, the smart water bottle also includes a light, speaker, or other component that prompts the user to drink in response to instructions from the external computing device. Compared to existing smart water bottles and software applications for monitoring hydration, some of which require manual tracking and inputting of liquid intake, inventive smart water bottles track liquid consumption automatically, more accurately, and more conveniently.

Inventive smart water bottles offer a number of other advantages as well. For instance, the external computing device can use information about the current weather and the user's physiology to estimate and provide a recommendation for a targeted fluid intake amount or rate. Specifically, the external computing device determines the user's approximate geographic location, e.g., from Global Positioning System (GPS) or other location measurements, and queries a weather server for the weather forecast at the user's geographic location. The external computing device can then estimate a customized target fluid intake amount or rate for the user based on the local weather (e.g., temperature, humidity, etc.), other information about the user's geographic location (e.g., the altitude), the user's previous or desired drinking habits, and/or previously entered or measured information about the user's physiology. The external computing device may also adjust the target fluid intake amount or rate based on the user's activity level, which can be estimated from measurements of the user's heart rate, etc.

Another advantage of inventive smart water bottles is the ability to make more accurate fluid level measurements at lower power consumption rates. Intermittent liquid level measurements (e.g., using a capacitive sensor or Hall Effect sensor) use less power than the continuous measurements made by fluid flow meters. A liquid level measurement can also be relatively accurate (e.g., to within 0.5 mL), depending in part on the shape and aspect ratio of the smart water bottle (e.g., wide and fat vs. tall and skinny). And by sensing when the bottle cap is removed and calculating differences in liquid level, the measurements are less sensitive to changes in the absolute liquid level (e.g., due to filling, spilling, or pouring) when the cap is off.

An Exemplary Smart Water Bottle

FIGS. 1A-1E show a container assembly 100 that can be used as a smart water bottle for tracking and prompting consumption of water or other fluids. The container assembly 100 includes a fluid container 102 with a removable cap assembly (lid) 104 is shown. The fluid container 102 can be made out of any translucent or transparent material, including glass or plastic. The glass or plastic may be textured, patterned, coated, embossed, colored, etc. as known in the art.

The fluid container 102 defines a water-resistant cavity that can hold liquid, such as water, which can be poured or sucked out of the container assembly 100 via a spout 105 in the removable cap assembly 104. The removable cap assembly 104 may screw, snap, or otherwise connect or couple to the fluid container 102 so as the form a watertight seal that prevents the liquid from leaking out of the assembled container assembly 100.

Figure 1B:
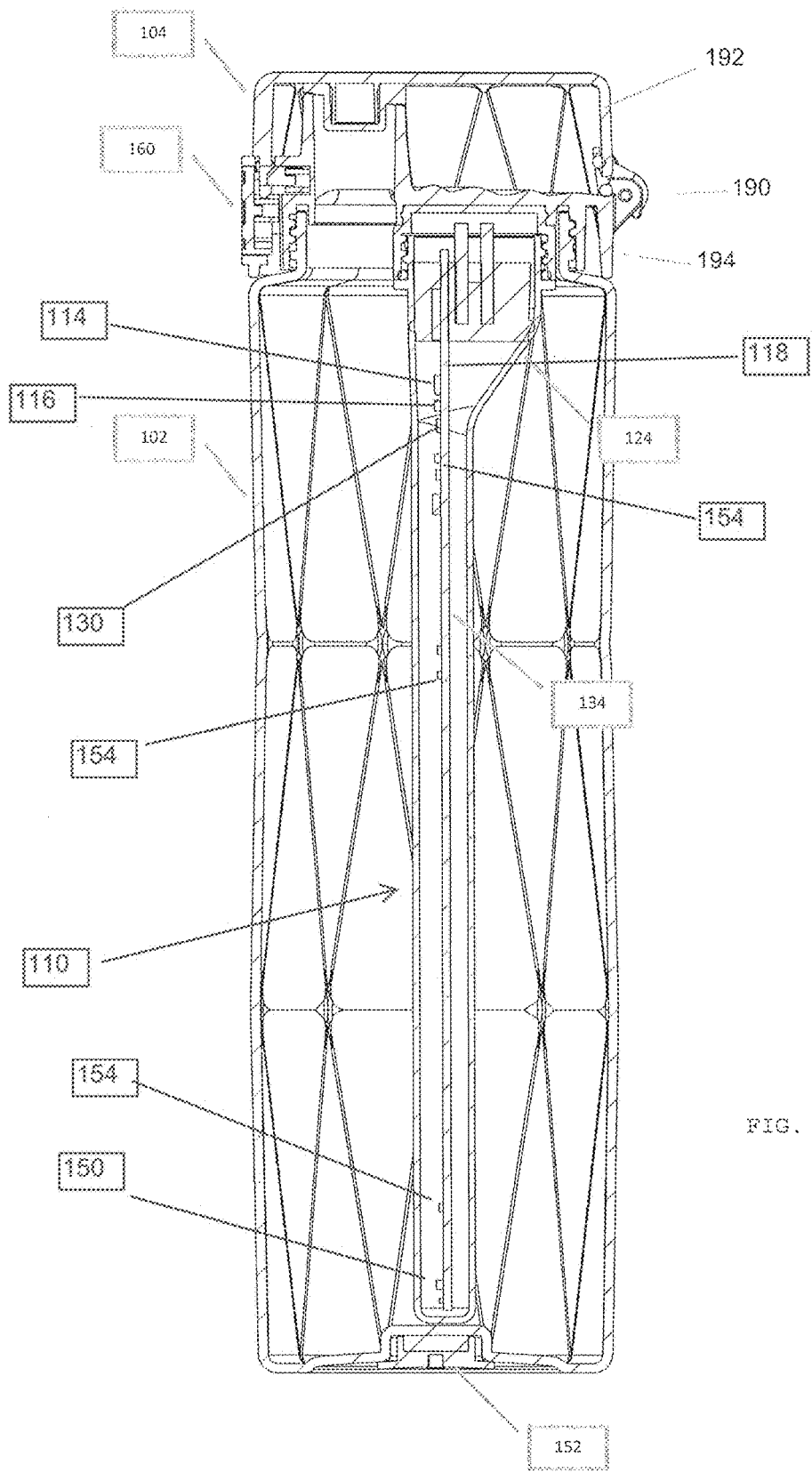

FIG. 1B shows a cross section of the container 100. The lid 104, which is composed of at least, but not limited to, one piece, is secured to the fluid container 102 and closed to prevent fluid from flowing out of the spout 105. An enclosure 124 containing an electronics assembly 134 extends from lid 104 inside the container 100 and into a cavity formed in part by the container 102. The enclosure 125 is positioned so that the electronics assembly 134 may extend into, but is insulated from, liquid in the container 100. When the lid 104 is properly secured to the container 102, the distal tip of the electronics assembly 134 is close to a magnet 152, such as a permanent ceramic magnet or electromagnet, embedded in or affixed to the bottom of the container 102. A Hall effect sensor 150 at the distal tip of the electronics assembly 134 senses the magnet 152 as described in greater detail below to provide an indication of whether the lid 104 is coupled to the container 102.

The electronics assembly 134 includes several electronic components mounted on a substrate 118, such as a piece of printed circuit board (PCB). These components include an antenna 114, a processor or controller 116 (e.g., a microcontroller unit (MCU)), an accelerometer 130, a proximity sensor 150, and one or more visual indicators 154. The electronics assembly 134 may also include or be coupled to a liquid level sensor 110 or flow rate sensor like those described in greater detail with respect to FIGS. 3-7.

The accelerometer 130 measures changes in the container's three-dimensional attitude and three-dimensional position. (Other embodiments may use or include a gyroscope to sense the container's position or attitude.) These measurements can be used to estimate or determine the position of the container assembly 100. The accelerometer 130 can also be positioned within or on the container 102 or the cap assembly 104.

The accelerometer 130 is used to determine the angle and orientation of the container 100, which may have an effect on the liquid level as sensed by the liquid level sensor 110. In an embodiment, the accelerometer 130 is used to determine if the container 100 is upright. If it is upright, a measurement is taken, otherwise a measurement is not taken. In another embodiment, the accelerometer 130 is used to determine an angle the container 100 forms with the ground, but the system only performs the measurement and calculation of the effective liquid height if the angle is within a specified range. Because the surface of the water is parallel to the ground regardless of angle, trigonometry can be used to determine the height of the liquid measured by the sensor to calculate the corresponding liquid height in the container 100 if the container 100 were vertical. In an embodiment if the container is within a specified range of angles, the height of the liquid would be calculated without adjustment. Beyond that range the measurement might not be taken, or if it is taken, the liquid height could be adjusted to compensate for the angle of the bottle during measurement.

The accelerometer 130 can be sampled by the processor 116 to retrieve data on a regular basis, e.g., every 2 seconds, to determine water bottle attitude. The specific interval (e.g., 2 seconds) is based on a balance between power consumption and measurement accuracy, and to ensure that a sufficient number of measurements are taken. For example, if a user pours in fluid into the bottle, and then drinks right away, the 2-second, for example can be sufficient to sample a measurement. The processor 116 can also poll the accelerometer 130 at a predetermined interval determined by, for example, the user or a coach, or any third party. The interval can be 1 second, 2 seconds, 5 seconds, 1 minute, 3 minutes, 5 minutes, 15 minutes, 30 minutes, 1 hour, 2 hours, 3 hours, 4 hours, 6 hours, and so on.

The interval may also change based on time of day, the user's schedule (possibly via synchronization with a calendar on the user's phone), and/or user preference or selection. For example, depending on the user's schedule, the sampling interval can be synchronized according to the user's desire. The interval can also be set to increase battery life or track activity level optimally. The interval can be automatically triggered to longer intervals if the battery on the smart bottle is low.

The proximity sensor or proximity switch 150 detects when the cap assembly and the bottle are not coupled together. As explained with respect to FIG. 2A, the proximity sensor or switch 150 can be implemented as a Hall effect sensor or switch that detects a magnet 152 in or near the bottom of the container 102. As readily appreciated by one skilled in the art, this proximity sensor or proximity switch 150 could also be implemented using any one of a number of other types of proximity sensors or proximity switches, including as an optical sensor or switch, for example, an ultraviolet (UV) or infrared (IR) sensor. Such a sensor could detect light emitted by a UV or IR light source placed in or near the bottom of the container 102. In these examples, the proximity sensor or switch 150 and the emitting source (e.g., magnet 152 or light source) are paired together to provide cap sensing functionality.

The electronics assembly 134 also includes one or more visual indicators 154. In an embodiment the visual indicator 154 could be one or more light sources, such as light emitting diodes (LEDs). The LEDs could be one color or multiple colors and may positioned at different locations in and on the container 100. As shown in FIG. 1B, for example, the visual indicators 154 are LEDs disposed on the electronic assembly 134 such that it roughly in the middle of the container 100. These visual indicators 154 can be used to provide visual reminders to the user to drink more as described in detail below with respect to FIGS. 8A-8F.

In operation, the processor 116 receives and processes information from the liquid level sensor 110 and the other electronic components within the water bottle 100. It stores this information in a memory (e.g., an internal or external buffer) and uses this information to estimate the change in the liquid level, the user's liquid consumption rate, and/or the total amount of liquid consumption over a given period. The processor 116's functions include collecting liquid level information or liquid flow data from the liquid level sensor 110, position and orientation data from the accelerometer 130, status of the cap (e.g., attached or separated) relative to the container 100 from the proximity sensor 150, and information including location and weather settings via the antenna 114 from an external device, such as a smartphone or a tablet. Once the data and relevant information have been collected, the processor 116 can send the data via the antenna 114 to the external device to report information, such as how much water the user has been drinking or how much water has been consumed at certain intervals, and determine recommendations, such as how much water the user should be drinking to meet the predetermined hydration target. In some embodiments, the processor 116 can determine the user's current consumption level or provide recommendations regarding the liquid consumption without relying on computational resources from an external device.

Depending on the electronic components, desired power consumption rate, battery level, etc., the data gathering by the processor 116 can take place periodically or can be triggered by certain events. For example, the processor 116 may poll the liquid level sensor 110 whenever it senses a change in the bottle's attitude or acceleration from the accelerometer 130, e.g., when the user tilts bottle. For example, the processor 116 may poll the accelerometer 130 intermittently (e.g., as discussed above with respect to the intervals for polling the liquid level sensor) and determine the orientation of the container assembly 100 based on acceleration measurements.

If the processor 116 determines that the bottle is within a predetermined ranges of orientations (e.g., vertical, ±15° from vertical, etc.), it polls the liquid level sensor and stores the change in the measurements in a buffer with the measurement time (e.g., time stamp). If there are no changes, the processor 116 may discard the measured data to conserve memory. The processor 116 may also use the acceleration data to adjust, compensate, or calibrate the liquid level measurement from the liquid level sensor 110.

The processor 116 can also compare hydration level during the day and the progress can be compared on a daily or weekly basis. The liquid level sensor 110 can also send the liquid level information to the processor 116 periodically (e.g., every 15 minutes, every 30 minutes, every hour, every two hours, etc.) or if no user activation takes place for a certain amount of time (e.g., 2 hours, 3 hours, etc.), which can be predetermined by the user.

The processor 116 may discount or stop measurements when the proximity sensor 150 indicates that the cap assembly 104 is not coupled to the container base 102. It may also poll the liquid level sensor 110 immediately after the proximity sensor 150 indicates that the cap assembly 104 has been coupled to the container base 102 in order to determine a new baseline liquid level.

In some instances, the processor 116 can sample continuous data from passive sensors. For example, when the accelerometer 130 measures changes in the container's three-dimensional attitude or three-dimensional position, it can report its position and/or orientation data to the microprocessor only when it detects motion. It also is possible for the accelerometer 130 to report its data periodically, e.g., to reduce power consumption by the accelerometer 130.

The processor 116 can share data with an external computing device, such as a smartphone, via antenna 114. In some embodiments, the processor 116 can also receive updates and/or instructions via antenna 114 from the external computing device. The transfer of measurements to the external computing device can take place when the smart bottle 100 is within the communication range of the external computing device. This range can vary depending on the specific technology being used via the antenna 114 and may range from inches to feet. When the smart bottle 100 is within the communication range of the external computing device, the external computing device can communicate, for example, by asking (1) whether the bottle has glowed (provided a visual prompt/indication to the user) and if so when it last glowed, or the duration since the last glow, and (2) by receiving hydration level and progress from the smart bottle. If the bottle has not glowed within a predetermined period (e.g., 5 minutes, 10 minutes, 15 minutes, etc., or a fraction of a preset interval between), then the external computing device commands the bottle 100 to glow to alert the user to drink more. By default, the smart bottle can be programmed to glow periodically no matter what. For example, the user can set the smart bottle to glow every 2 hours.

When the processor 116 or external device determines the status of the user's liquid consumption level, the processor 116 can use the LED 154 to notify the user of his or her liquid consumption level. The processor 116 can also use blinking LEDs (indicators 154) to let the user know when or how often to drink from the container. Some of the possible ways the processor 116 can display the notification include causing the LED 154 to blink, pulsate, or light up (glow) based on determination (different colors, patterns, etc.). The processor 116 and/or the external device can prompt alerts comprising text displays, noise (e.g., an audible beep), vibration, etc., using a display, vibrator, or speaker on the water bottle container 100 or the external device. In some cases, the processor 116 may cause an actuator to flip open the cap, e.g., to remind the user to drink more.

In some instances, the processor 116 can be set to prompt the user to drink at certain intervals or when the user does not follow the predetermined hydration regime. In some instances, the processor 116 conducts more measurements and sends or displays prompts to hydrate more frequently if the processor 116 determines that the user should be more hydrated. The processor 116 can be pre-programmed to tailor sensing of the liquid level and displaying or alerting of notifications according to the time of day (e.g., during the day when the user is active or when the usually is asleep or at night regardless of what the user is doing).

In some embodiments, when the liquid level is low, the processor 116 can display a notification to refill the container 100 with liquid. This notification can be a visual indication, audible indication, or mechanical vibration. This notification can be different from other notifications where the user is prompted to follow the hydration regime.

Figure 1C:
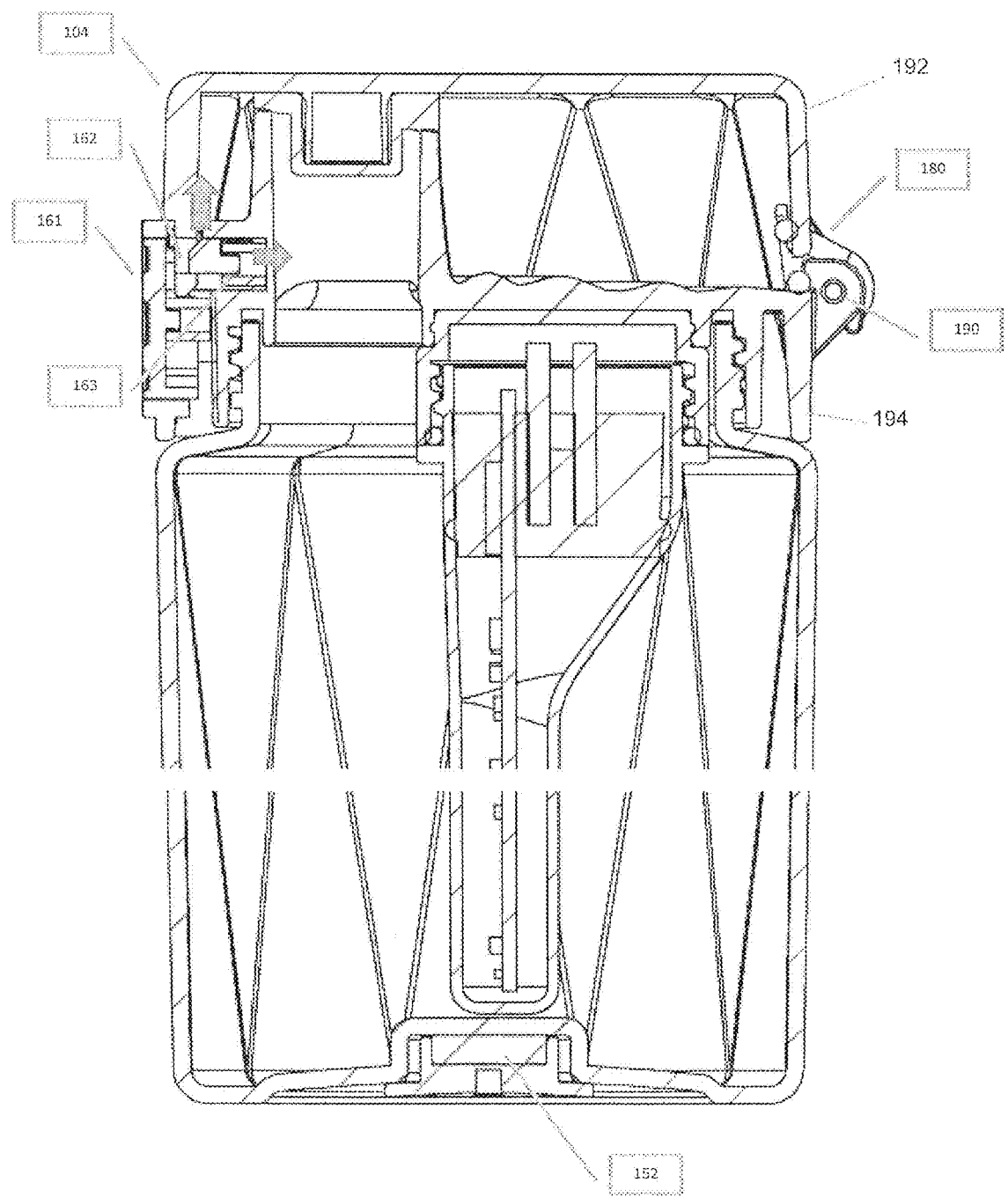
Figure 1D:
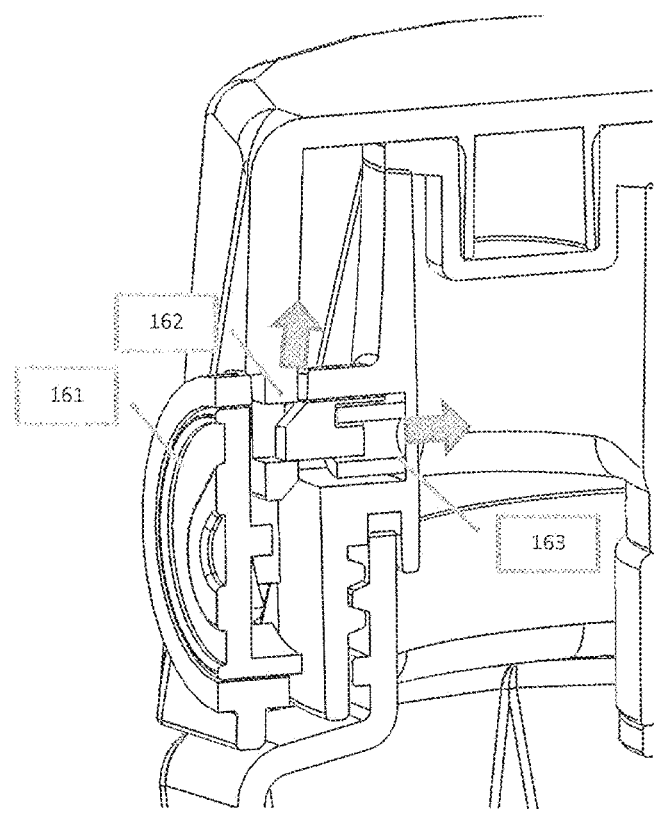
FIGS. 1D and 1E show cutaway views of the smart water bottle lid shown in FIGS. 1A-1C.
Figure 1E:
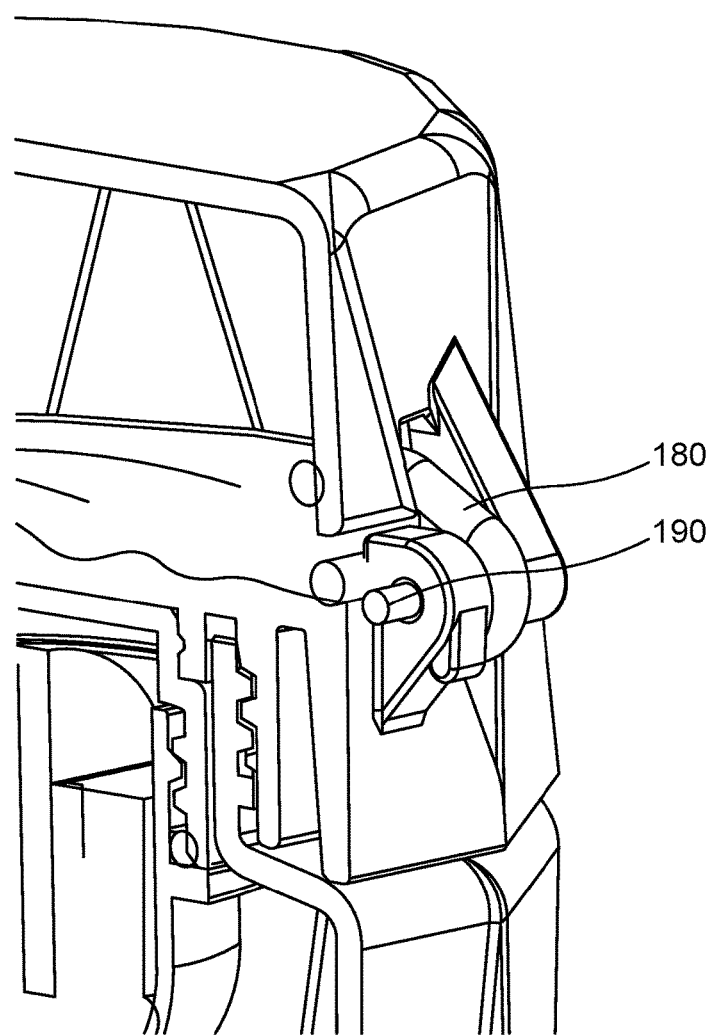

FIGS. 1C, 1D, and 1E are cutaway views that show a latch mechanism 160, a spring or elastic band 180, and a hinge 190 for opening the lid 104 and keeping the lid 104 closed. The hinge 190 connects an upper piece 192 with a lower piece 194 of the lid 104. Closing the lid 104 (e.g., by pushing the upper piece 192 towards the lower piece 194 about an axis defined by the hinge 190) places the spring or elastic band 180 in tension and engages the latch mechanism 160, which keeps the spring 180 in tension and the lid 104 closed. Actuating the latch mechanism 160 releases the spring 180, causing the lid 104 to pop open. More specifically, FIGS. 1D and 1E show that pushing a button 161 towards the longitudinal axis of the smart water bottle 100 engages another spring 163, which in turn causes a latch 162 to disengage, releasing tension on the spring or elastic band 180.

The Lid/Cap Assembly

Figure 2A:
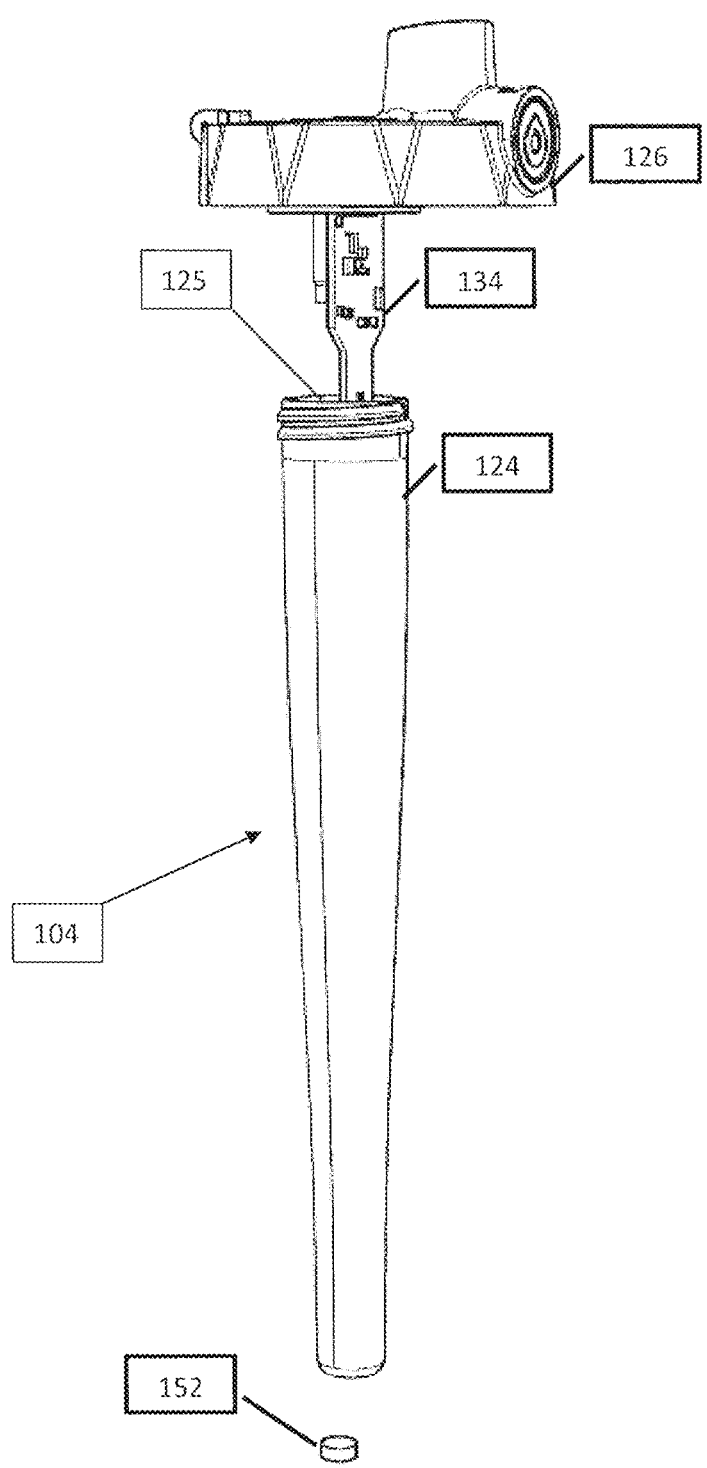
FIG. 2A is a perspective view of the assembly of the electronic system and cap of a liquid level sensor.

FIG. 2A is a partially exploded view of the cap assembly (lid) 104 shown in FIGS. 1A-1E. In this embodiment, the liquid level cap assembly 104 includes at least two pieces: a housing or capsule 124 and an upper cap or lid 126, which can be screwed or otherwise affixed together to enclose a cavity 125 defined by the fluid container 102. The housing 124 and upper cap 126 may be affixed by any number of fastening methods, including, by way of example only and not by way of limitation, threading, screws, nuts and bolts, glue, snap-fittings, welding, or the like.

The inside of the cavity 125 formed by the housing 124 and the upper cap 126 can include a power supply and/or some or all of the electronics assembly 134. The housing 124 protects the electronics assembly 134 without significantly impeding its ability to measure and process information about the liquid level.

Sensing Removal of the Smart Water Bottle Lid

FIG. 2A also shows the magnet 152 that can be affixed or coupled to the distal tip of the housing 124. A Hall effect transducer (not shown) at or near the distal tip of the housing 124 produces an output voltage whose amplitude varies in response to variations in applied magnetic field, including the field generated by the magnet 152. In other words, the Hall effect sensor can be used as a proximity sensor that senses the permanent magnet 152 placed on or embedded in the bottom of the container 102. (Alternatively, the magnet can be in the housing 124 and the Hall effect sensor 152 may be in or on the container 102.) When the Hall effect sensor 150 moves with respect to the permanent magnet 152, e.g., because the cap 104 is being screwed onto or unscrewed from the container 102, the Hall effect sensor 150 produces a voltage signal representative of the movement. This signal—along with a possible change in the liquid level—can be used to infer that the bottle is being filled with or emptied of liquid.

Battery Enclosure

Figure 2B:
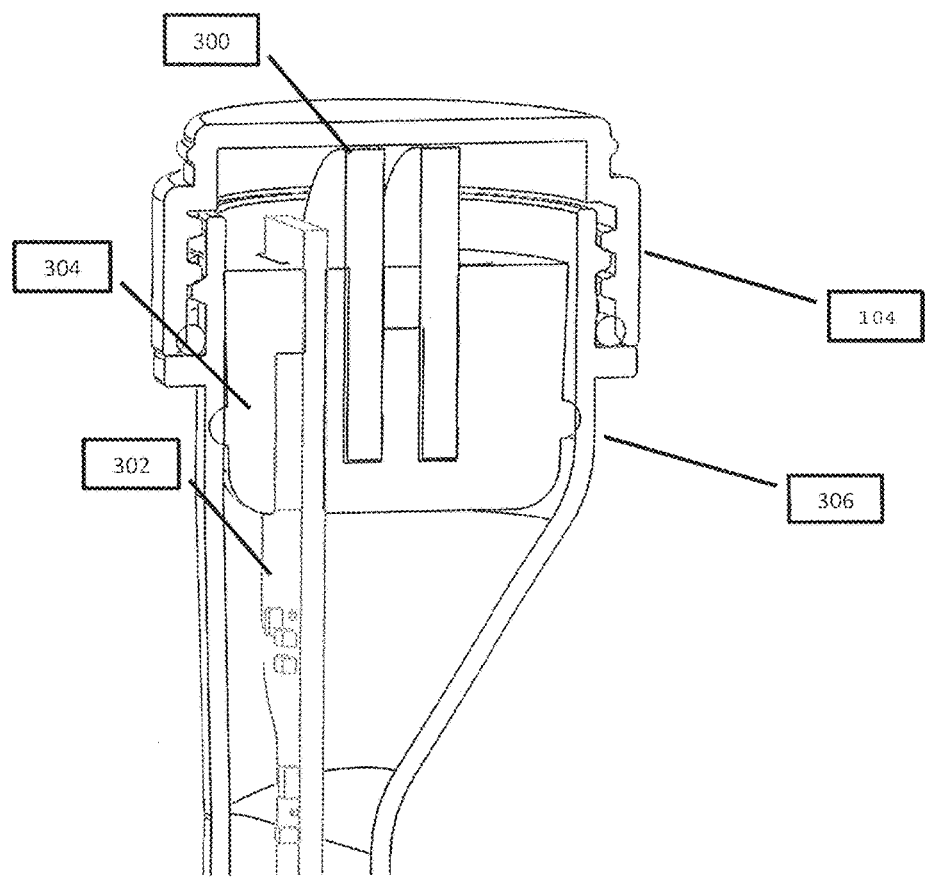
FIG. 2B is a cutaway view of a battery assembly coupled to the electronic system and cap shown in FIG. 2A.

FIG. 2B is a view of a battery securement and insulation assembly 306 for powering electronics in and coupled to the lid 104. The battery securement and insulation assembly 306 defines an enclosure that is insulated (e.g., watertight and airtight) from both the interior of the larger container and the rest of the electrical assembly. The entire assembly 306 can be formed of any number of pieces that define a watertight and airtight enclosure. In this case, a plug 304 separates the interior of the enclosure 306 into two volumes. In one volume, the battery 300 is secured. Conductive material provides a connection between the battery 300 and the electronic assembly 302 in the second volume without compromising the airtight seal formed by the plug 304 between the two enclosing volumes. An electronic assembly 302 can be embedded inside the plug 304, with conductive material providing a connection to the battery 300 without compromising the airtight seal.

Capacitive Liquid Level Sensors for Smart Water Bottles

FIG. 3 is a view of a capacitive liquid level sensor 300 suitable for use with the container 100 shown in FIGS. 1A-1E and the cap assembly 104 shown in FIGS. 2A and 2B. The capacitive level sensing system 300 includes electrodes 310a and 310b (collectively, electrodes 310), each of which extends along the length of the capacitive liquid level sensor 300. Alternatively, the electrodes 310 could be formed as an array of electrodes spread along the length of the level sensing electrical system 300.

In one embodiment, the electrode structure 132 is isolated from the liquid inside the container by enclosing the electrode structure 132 in a barrier or housing 124, which insulates the electrode structure 132 from a direct contact with liquid in the container 102. The barrier or housing 124 can be a physical capsule providing an air tight cavity when coupled with the upper cap 126 (FIG. 2A). Alternatively the barrier or housing 124 can be a coating that seals the electronics assembly 134 against the liquid. The capacitance measurement can be calibrated around the collective capacitance provided by the combination of capacitance components from the air, the electrode substrate, and plastic housing.

In some embodiments, the electrode structure 132 can be exposed to liquid to increase accuracy of the measurements. Exposing the electrode structure 132 to liquid can decrease service life of the electrodes via degradation processes, such as corrosion. The exposed electrode structure 132 can also be harmful to the user if the corroded metal or part is ingested.

As shown in FIG. 3, the housing 124 and liquid level sensor 300 are positioned such that they run roughly along the longitudinal axis of the container assembly 100 when the cap assembly 104 is screwed into the container 102. As a result, the liquid level sensor 300 runs roughly through the centroid of the surface of the liquid inside the container assembly 100, even if the container assembly 100 is tilted, so long as the bottom of the container 102 is completely covered in liquid. If the container 102 is rotationally symmetric its longitudinal axis, the liquid level sensor 300 should measure the liquid level accurately if the bottom of the container 102 is completely covered in liquid. The exact ranges of angles over which this holds true depends on the dimensions of the container 102 and the amount of liquid inside the container 102 (the emptier the container 102, the smaller the range of angles).

In other examples, the housing 124 and liquid level sensor 300 may be positioned so that run along an axis that is parallel to, skew to, or intersects with the longitudinal axis of the container 102. The housing 124 and liquid level sensor 300 can also be integrated with the container 102 or connect directly to the container 102 instead of connecting to the cap assembly 104. And in some cases, the liquid level sensor 300 can be covered with a protective (waterproof) coating and inserted directly into the liquid instead of being enclosed in a housing. Certain implementations of the liquid level sensor 300 can be in direct contact with the water.

In operation, the liquid level sensor 300 measures the capacitance between the electrodes 310. This capacitance depends on the liquid level: the capacitance increases roughly linearly as the liquid level goes up and decreases as the liquid level goes down. Initially, the liquid level sensor 300 can be calibrated for a particular liquid (e.g., water) by measuring the capacitance between the electrodes 310 as a function of liquid level for that liquid. This calibration routine can be done for different liquids to correct for the types or properties of the different liquids. After repeated measurements, a correlation factor (or a multiplier) can be empirically determined for the entire electrodes 310 or to specific regions of the electrodes 310. The empirically determined correlation factor or multiplier from the measurements can be then made to correct for different regions of the water bottle. By using this approach, the liquid level inside the water bottle can be more accurately determined in real life use.

Similarly, different regions of the water bottle can be repeated calibrated and the calibrated results from each of the regions can be reconstructed or combined to provide an overall calibration profile or "curve" to potentially correct for measurement discrepancies though the entire of range of liquid level inside the water bottle.

The processor 116 uses the capacitance changes measured by the electrodes 310 due to the changes in the liquid level within the container to estimate the user's liquid consumption. The measurement of liquid level is enabled because the difference in capacitance values can be correlated to the difference in liquid volumes, e.g., in fluid ounces or milliliters. The processor 116 can also perform a correlation between percentage of filled volume and absolute volume, and the processor 116 then transmits, to the external software application, the data in fluid ounces or milliliters.

Hall Effect Liquid Level Sensors for Smart Water Bottles

Figure 4:
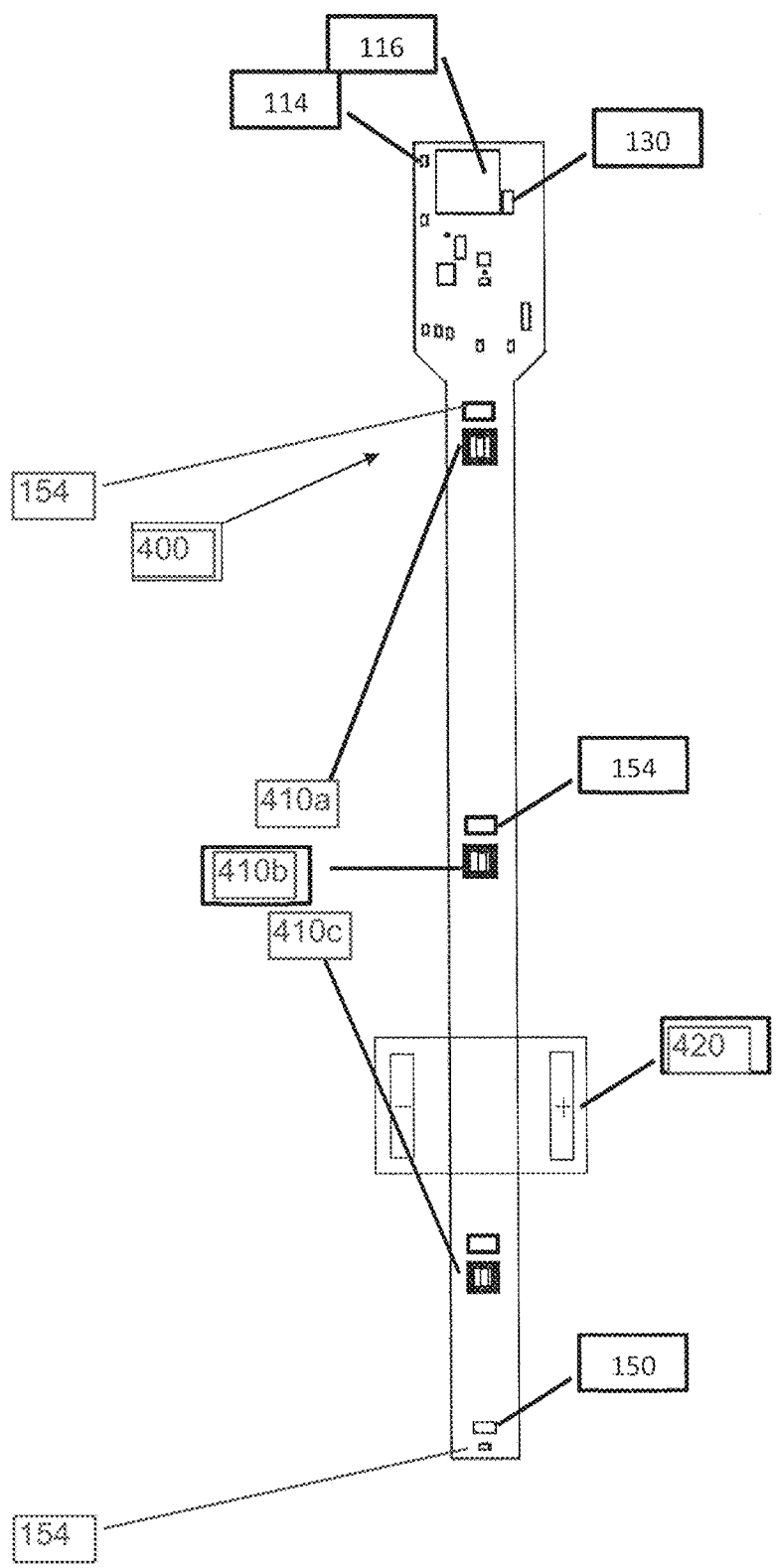
FIG. 4 shows a Hall Effect liquid level sensor suitable for use with the container shown in FIG. 1A and the cap shown in FIG. 2A.

FIG. 4 shows a Hall effect liquid level sensor 400 suitable for use with the container 100 shown in FIGS. 1A-1E and the cap assembly 104 shown in FIGS. 2A and 2B. The Hall effect liquid level sensing system 400 includes an array of Hall effect sensors 410a, 410b and 410c (collectively, sensors 410) mounted as an array spread along the length of the level sensing electrical system 400, as shown in FIG. 4.

In some embodiments, the sensors 410 can be isolated from the liquid inside the container by enclosing or sealing the sensors 410 in a barrier or housing 124, which insulates the electrical system 400 from a direct contact with liquid in the container 102. The barrier or housing 124 can be a physical capsule providing an air tight cavity when coupled with the upper cap 126 as shown in FIG. 2A. Alternatively the barrier or housing 124 can be a coating that seals the electronics assembly 400 against the liquid.

As shown in FIG. 4, the housing 124 and liquid level sensor 400 are positioned such that they run roughly along the length (longitudinal axis) of the container assembly 100 when the cap assembly 104 is screwed into the container 102. As a result, the Hall effect liquid level sensor 400 runs roughly through the centroid of the surface of the liquid inside the container assembly 100, even if the container assembly 100 is tilted, so long as the bottom of the container 102 is completely covered in liquid. If the container 102 is rotationally symmetric its longitudinal axis, the liquid level sensor 400 can still measure the liquid level accurately if the bottom of the container 102 is completely covered in liquid. The exact ranges of angles over which this holds true depends on the dimensions of the container 102 and the amount of liquid inside the container 102 (the emptier the container 102, the smaller the range of angles).

In other embodiments, the housing 124 and liquid level sensor 400 may be positioned so that they run along an axis that is parallel to, skew to, or intersects with the longitudinal axis of the container 102. The housing 124 and liquid level sensor 400 can also be integrated with the container 102 or connect directly to the container 102 instead of connecting to the cap assembly 104. And in some cases, the liquid level sensor 400 can be covered with a protective (waterproof) coating and inserted directly into the liquid instead of being enclosed in a housing 124. In some embodiments, the liquid level sensor 400 can be in direct contact with the water.

In operation, the liquid level sensor 400 measures the location of the float 420 by measuring the magnetic flux variations detected by the Hall effect sensors 410. For example, if the liquid level is between sensors 410a and 410b, as the liquid level decreases due to consumption by the user, the float 420 moves down from the location of sensor 410a to the location of sensor 410b. The magnetic flux measured by the sensor 410a and the magnetic fluxes measured by the sensors 410a and 410b will change by amounts corresponding to the distances between the float 420 and the sensors 410a and 410b. These changes in the magnetic fluxes measured by the adjacent sensors can provide the location of the float 420, which corresponds to the location of the top surface of the liquid inside the container 100. By using the relative magnetic flux values, the liquid level can be measured as the liquid level increases or decreases.

The processor 116 can then use the magnetic flux variations measured by the sensors 310 to estimate the user's liquid consumption. The measurement of liquid level is enabled because the difference in the magnetic flux values can be correlated to the difference in liquid volumes, e.g., in fluid ounces or milliliters. The processor 116 can also perform a correlation between percentage of filled volume and absolute liquid volume, which the processor 116 can then transmit the data in fluid ounces or milliliters to the external software application or device.

Liquid Flow Meters for Smart Water Bottles

Figure 5A:
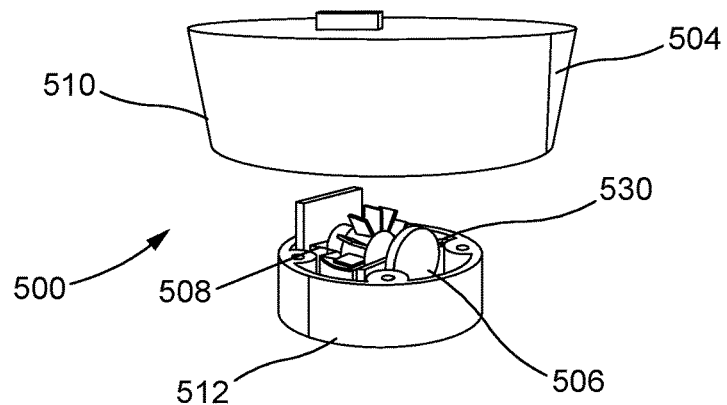
FIG. 5A is an exploded view of a liquid flow-rate sensor cap assembly suitable for use with the container of FIG. 1A.
Figure 5B:
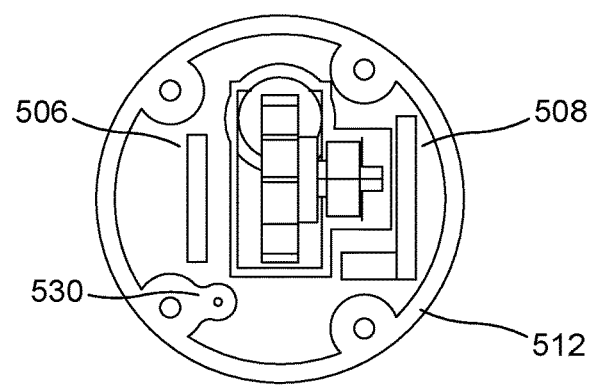
FIG. 5B is a top view of the liquid flow-rate sensor cap assembly of FIG. 5A.

FIG. 5A is an exploded view of an alternative removable cap assembly 504 of the container assembly 100 with a fluid-flow sensing system 500. FIG. 5B is a top view of the interior of the removable cap assembly 504 with contained electronic components. In this embodiment, the removable cap assembly 504 is composed of at least, but not limited to, two pieces, an upper cap or lid 510 and a fluid-flow sensor housing 512 that are coupled together to create a hollow, water-resistant cavity. The upper cap 510 and the fluid-flow sensor housing 512 may be coupled by any number of fastening methods, including, by way of example only and not by way of limitation, threading, screws, nuts and bolts, glue, snap-fittings, welding, or the like.

In an embodiment, the cap assembly 504 with a fluid-flow sensing system features a small through-hole 530 that runs through the interior of the container 100 (not shown) to the exterior of the removable cap assembly 504 to increase the rate and improve the quality of liquid flow by providing an additional channel for air to enter the container 100. The inside cavity formed by the upper cap 510 and the fluid-flow sensor housing 512 may include a power supply 506 and a fluid-flow sensing system 500 for measuring liquid flow. The fluid-flow sensing system 500 contains a sensor assembly, shown in FIG. 5C, capable of determining the rate of liquid flow out of the container, a power source, and a system for wirelessly transmitting and/or receiving data (e.g., using the Bluetooth protocols).

Figure 5C:
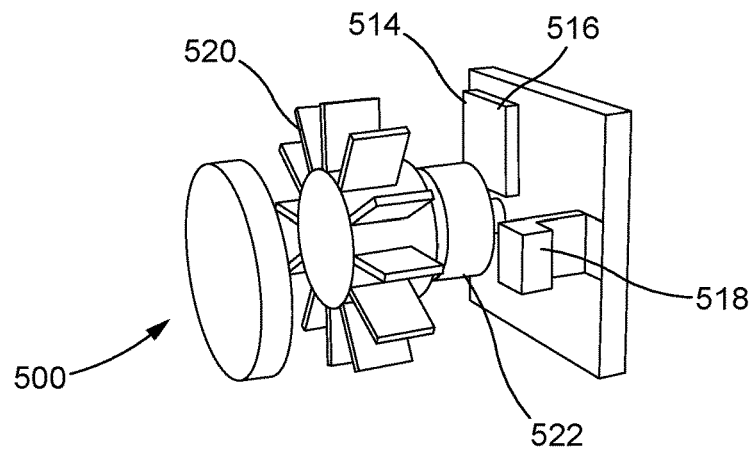
FIG. 5C is a perspective view of the liquid flow-rate sensor of FIGS. 5A and 5B.

FIG. 5C is an exploded view of the fluid-flow sensing system 108 containing the sensor assembly for detecting liquid flow, according to an embodiment. In an embodiment, there are four components to the fluid-flow sensing system 108. The first component is a communication device such as an antenna 114 for the wireless transmission and reception of data (e.g., using the Bluetooth protocols). The second component is a microcontroller unit (MCU) 516 to process the level sensing information before transmission. The third component is a proximity sensor or switch 518. The fourth component is an impeller 520. In an embodiment, the impeller 520 features an emitting source 522 affixed to, embedded in, or otherwise synchronized in rotation with the impeller 520.

In this embodiment, the flow rate of a fluid leaving the container can be determined. The rotation of the impeller 520 and the resulting rotation of the emitting source 522 results in the proximity sensor or switch 518 generating a signal. This signal transmitted via the communication device 514 to a software application on an external device. In an embodiment, an integer corresponding to the number of rotations of the impeller is transmitted to the external software application, which correlates the number of rotations with the flow rate. In an embodiment, the flow rate is expressed in milliliters or fluid ounces over any unit of time. In an embodiment, the microcontroller 516 performs the correlation and transmits the flow rate to the external software application. The data from the microcontroller 516 is transmitted to and from software applications on external devices including, but not limited to, smartphones, tablets, laptops, smartwatches, and other types of computers.

Ultrasonic Liquid Level Sensors for Smart Water Bottles

Figure 6:
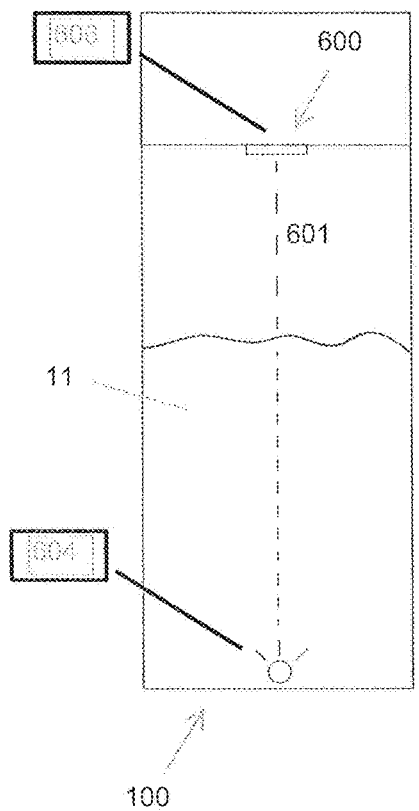
FIG. 6 shows an ultrasonic liquid level sensor suitable for use with the container shown in FIG. 1A.

FIG. 6 shows an ultrasonic sensor system 600 that measures the fluid (e.g., water) level within the container by sensing an ultrasonic wave 601 that reflects off or is transmitted through the surface of the fluid. In this case, the sensor system 600 includes a transducer 606 in or on the cap 104 and a sensor 604 in or on the bottom of the container 100. In operation, the transducer 606 generates the ultrasonic wave 601, which propagates through liquid 11 in the container 100 to the sensor 604. In response to detecting the ultrasonic wave 601, the sensor 604 produces a signal that varies in a way that can be correlated to liquid level.

Infrared Liquid Level Sensors for Smart Water Bottles

Figure 7:
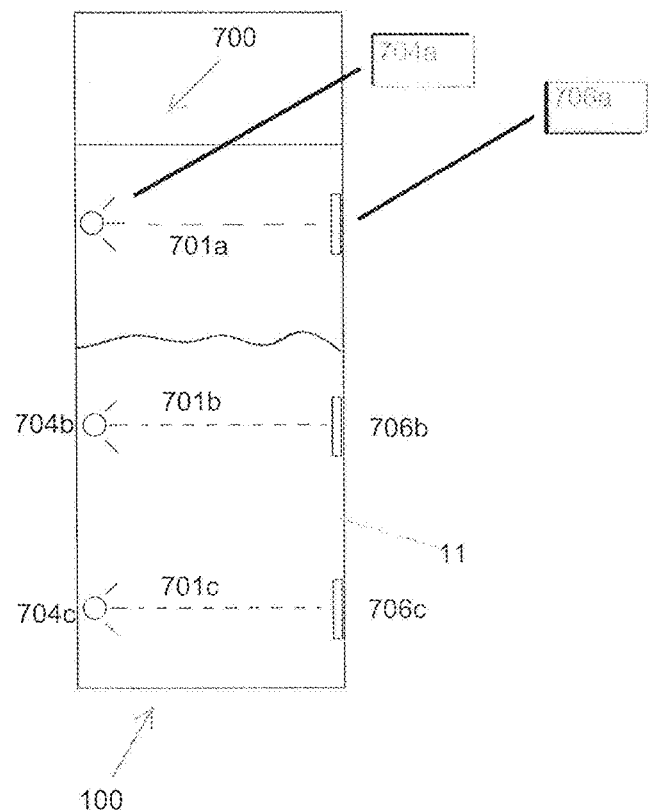
FIG. 7 shows an infrared liquid level sensor suitable for use with the container shown in FIG. 1A.

FIG. 7 shows an infrared (IR) liquid level sensor 700 that includes several infrared light source 704*a*-704*c* (collectively, IR light sources 704) and several corresponding infrared light receivers 706*a*-706*c* (collectively, IR light receivers 706). Each infrared light source 704 is placed opposite the corresponding infrared light receiver 706 and perpendicular to the surface of the liquid 11 when the container 100 is in an upright orientation. In operation, each IR light source 704 emits a continuous-wave or pulsed beam of infrared light 701 towards the corresponding IR receiver 706. As the liquid level varies, the measurements taken by the receivers 706 vary in a way that can be correlated to liquid level. These measurements can be correlated with angle/orientation measurements made by the accelerometer 130 to estimate the amount of fluid in the container and/or the change in fluid level over time (e.g., since the last measurement).

Visual Feedback Via a Smart Water Bottle

FIGS. 8A-8F are illustrations of exemplary visual notifications the smart water bottle 100 can provide to let the user know of the status of the user's hydration level. The visual notification can be used to prompt or remind the user to drink from the smart water bottle, to refill the smart water bottle, to replace the battery, to stop drinking, etc. The visual notifications may also indicate the status of a wireless communication link or data transfer between the smart water bottle and a smartphone or other electronic device. Among many possible locations on the smart water bottle, the visual notifications can be displayed with LEDs and/or other light sources mounted in or on the side of the smart water bottle, on the top of the smart water bottle cap, on the latch mechanism, and/or throughout the entire bottle to inform the user of his or her hydration status, hydration goal, etc. If the smart water bottle is translucent and the LEDs are inside the smart water bottle, the visual indication may appear as a soft "glow" that may pulsate one or more times.

As illustrated in FIG. 8A, a blinking light 802 (provided, for example, a single blinking indicator 154) in the middle of the water bottle 100 can be used as a notification for the user to drink more water to stay within the programmed hydration level. The position of the blinking light 802 within the water bottle 100 may include a target consumption volume or level (e.g., "drink until the water level is even with the light"). In other embodiments, the indicators 154 may be used to display a particular volume of liquid to be consumed. Likewise, the blinking rate or LED color may indicate a target liquid consumption rate, with faster blinking corresponding to a higher target rate.

Lighting up an array of LEDs 154 causes the smart water bottle 100 to emit a "glow" 804 as shown in FIG. 8B. This may indicate that the user needs to refill the water bottle 100. In some notification schemes, one or more of the indicators 154 can be used to display a gradient in the intensity—a gradient glow—indicative of the user's estimated hydration level. For example, some or all of the indicators 154 that are mounted along the electrical system can be used to indicate any variety of metrics (i.e., to show the degree of lagging with respect to a given hydration target). In other notification schemes, a plurality of the indicators 154 may be used to indicate that the user has not consumed liquid from the bottle for a specify amount of time, and thus may not meet the hydration target.

Figures 8C, 8D:
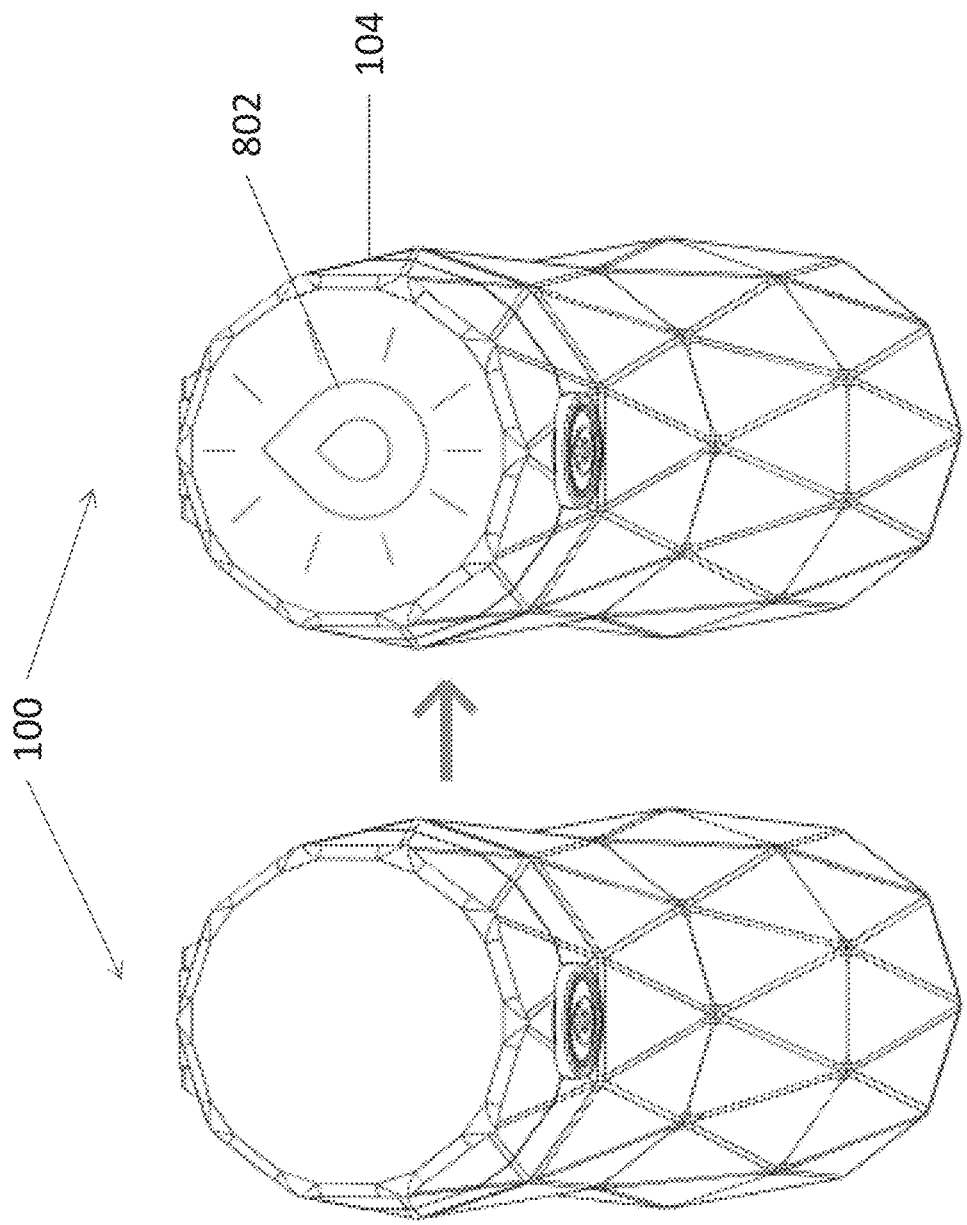
Figure 8F:
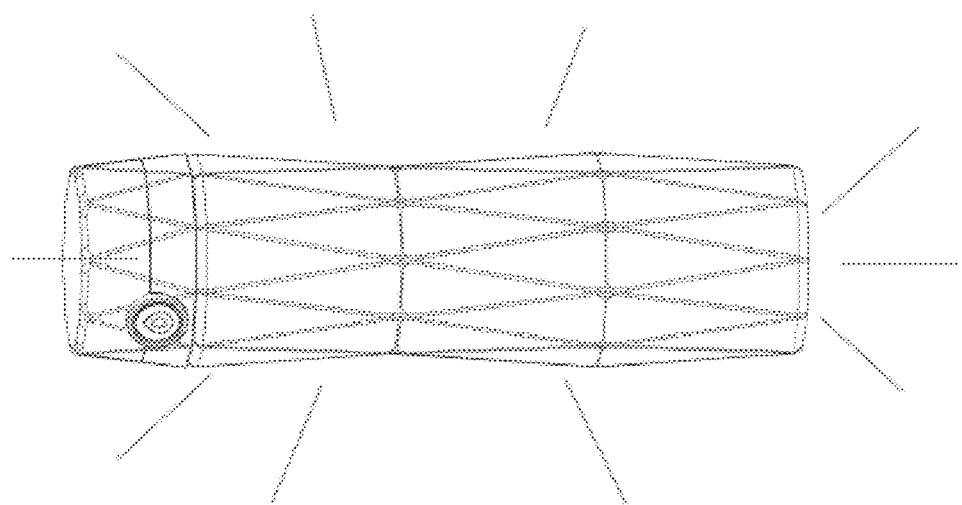
Figure 8E:
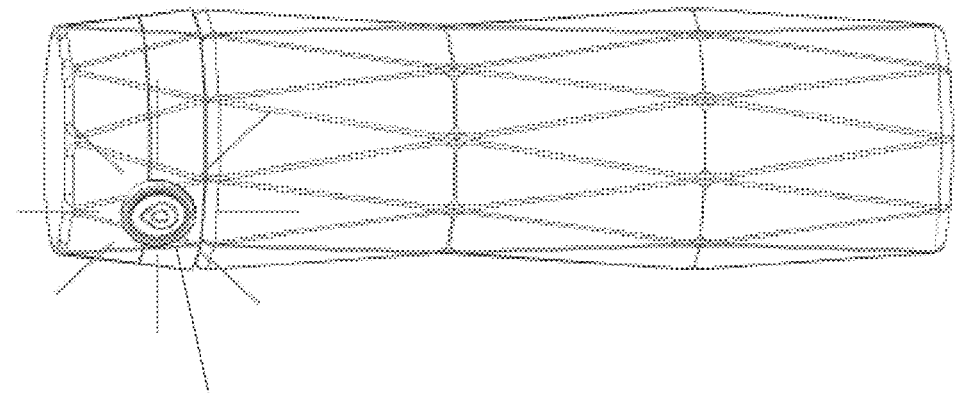

FIG. 8C and FIG. 8D illustrate how LEDs in or on the cap 104 of the smart water bottle 100 may provide a glowing symbol 806, e.g., to indicate that the user needs to drink or that the smart water bottle 100 is communicating with a smartphone or other wireless device. The glowing symbol may also be located on the latch 160 as shown in FIG. 8E. Again, the color and/or intensity may vary to provide different messages (e.g., steady illumination may indicate a connection, fast blinking may indicate data transfer, slow blinking may indicate a firmware upgrade, etc.). The cap 104 may have different symbols to indicate different status conditions (e.g., recharge battery, refill container, download hydration targets or weather data, upload liquid consumption data). And in some cases, the entire water bottle 100 may glow as shown in FIG. 8F.

In some embodiments, the user can manually activate the indicators 154 to glow to show the progress towards a completed liquid consumption goal. The indicators 154 can ask be automatically activated when the liquid level has not changed for a predetermined period, notifying the user that the current hydration level for water consumption is not adequate and that more water consumption maybe required to stay on target.

Smart Water Bottle Systems and Apps

Figure 9A:
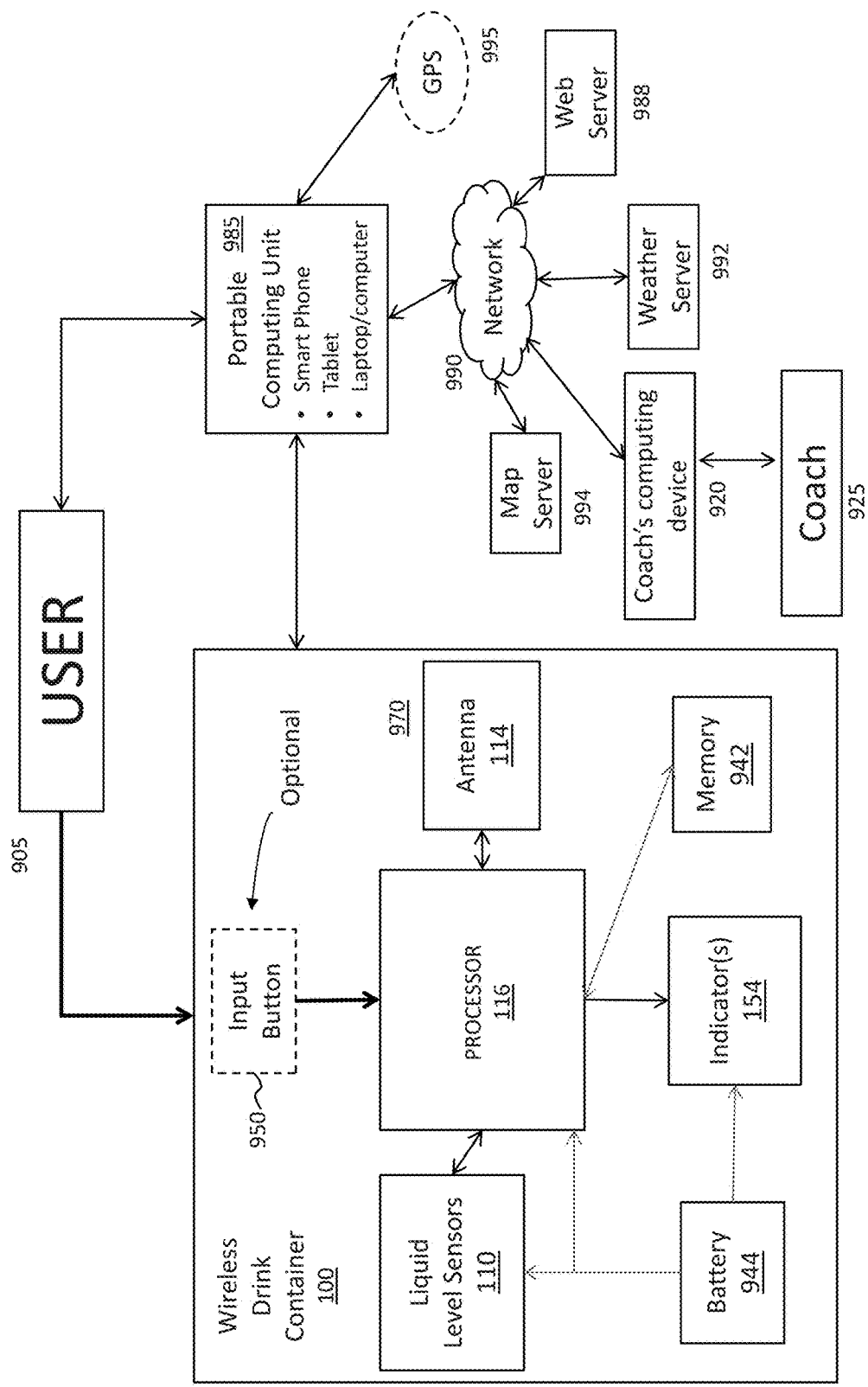
FIG. 9A is a block diagram illustrating components of the smart water bottle and interconnections between the smart water bottle and a portable computing device, which is further connected to a larger network.

FIG. 9A shows a schematic illustration of a system including a smart water bottle 100 disclosed above. Besides the smart water bottle 100, the system also includes one or more of the computing devices 985, such as smartphones, tablets, smartwatches, or computers, which may be coupled to other computing devices via a computer network 990, such as the Internet. A user 905 may interact with the smart water bottle 100 and other device(s) 985 as described in greater detail below.

FIG. 9A shows the water bottle 100 and electronic components within the water bottle 100. The various components in the drink container 100 include a processor 116, one or more liquid level sensors 110, an antenna 114 for outside communication, one or more indicators 154 (e.g., LEDs), a memory unit 942, a battery unit 944, and optionally a user input 950. Since the various electronic and sensing components within the water bottle have been described in full detail with reference to FIGS. 1-7.

The smart water bottle 100 can send data to and receive data and instructions from the (portable) computing device 985 via as a local area network, like a Wi-Fi network, a hotspot, a personal network or curated company network, or a wide area network, like the Internet (world wide web). In turn, the computing device 985 can communicate via a wide-area network 990 with various dedicated web servers 988, including but not limited to a weather server 992 and a map or location server 994. The computing device 985 may also receive position information directly from a positioning system 995, such as the Global Positioning System (GPS) or the Global Navigation Satellite System (GLONASS). In alternative embodiments, the smart water bottle 100 may communicate with the weather server 992, map server 994, and/or GPS 995 directly or via the network 990 in addition to or instead of communicating with them via the computing unit 985.

Figure 9B:
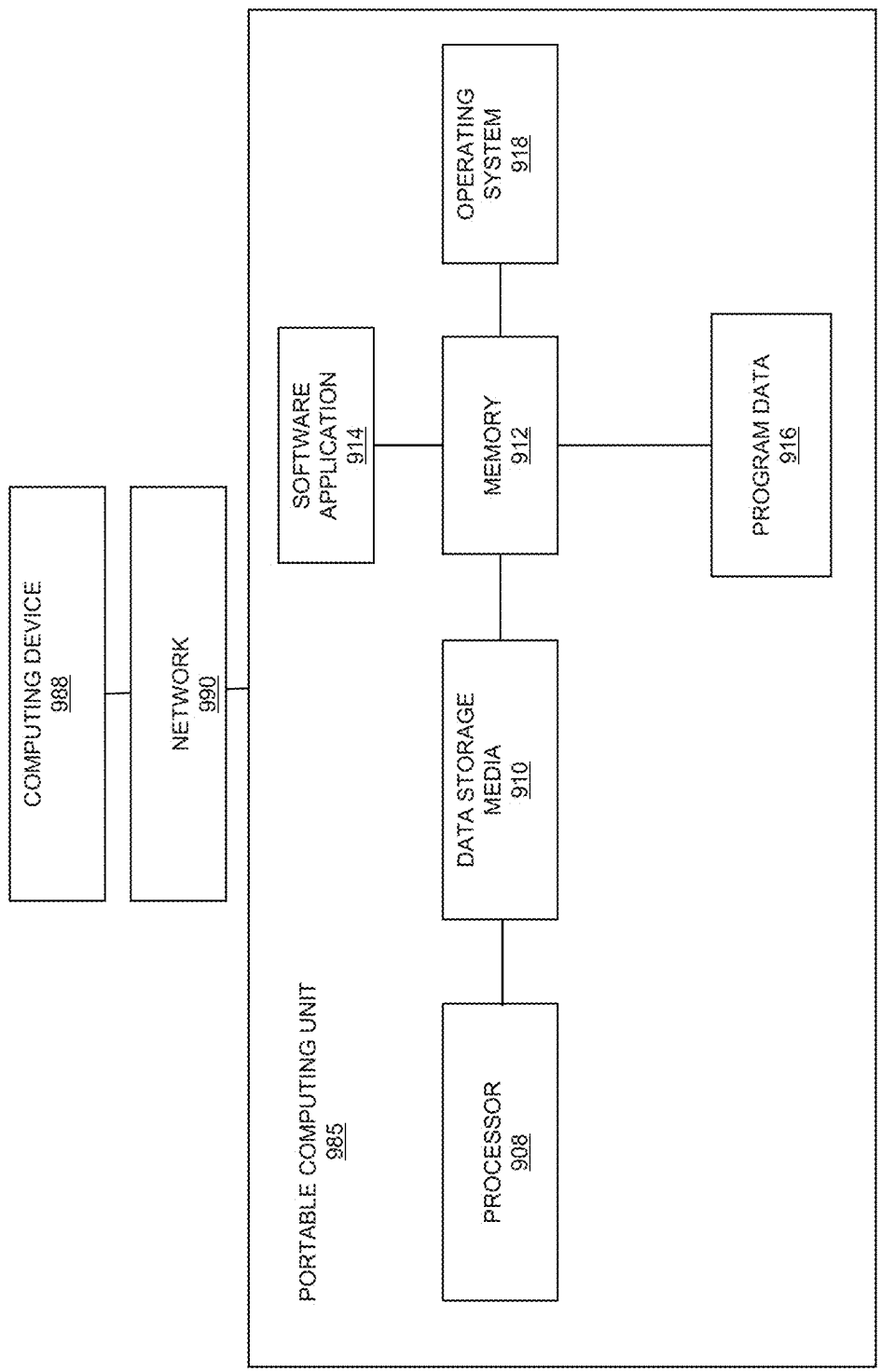
FIG. 9B is a block diagram illustrating an example of a computing system suitable for tracking fluid consumption from the container of FIG. 1A.

FIG. 9B is a block diagram illustrating the connections between internal components of the external computing device 985, which is connected to one or more servers 988 via a network 990. The external computing device 985 can be located in the residence or place of business of the user 905. The external computing device 985 can be a mobile device, such as a smart phone, tablet, smart watch, or other mobile devices. The external computing device 985 can be a stand-alone computing device or a networked computing device that communicates with one or more other computing devices or dedicated servers 988 across the network 990. The additional computing device(s) or server 988 can be located remotely away from the external computing device 985, but all are configured for data communication across the network 988.

Both the external computing device 985 and the server 988 can include at least one processor or processing unit 908 and a system memory 912. The processor 908 is a device configured to process a set of instructions. The system memory 912 may be a component of processor 908 or separate from the processor 908. Depending on the exact configuration and type of computing device, the system memory 912 may be volatile (such as Random Access Memory), non-volatile (such as Read-Only Memory, flash memory, etc.) or some combination of the two. System memory 912 typically includes an operating system 918 suitable for controlling the operation of the external computing device 985. The system memory 912 may also include one or more software applications 914 and may include program data 916.

The external computing device 985 can include additional features or functionality, including attaching to additional data storage devices 910 (removable and/or non-removable) such as, for example, magnetic disks, optical disks, or tape. Computer storage media 910 may include volatile and nonvolatile, removable and non-removable media implemented in any method or technology for storage of information, such as computer readable instructions, data structures, program modules, or other data. System memory, removable storage, and non-removable storage are all examples of computer storage media. Computer storage media 910 can include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing device 902. An example of computer storage media 910 is non-transitory media.

In some embodiments, the external computing device 985 can be a personal computing device that is networked to allow the user to access and utilize the hydration system disclosed herein from a remote location, such as in a user's home, office or other location. In some embodiments of the external computing device 985, system operations and functions are stored as data instructions for a smart phone application. A network 990 can facilitate communication between the external computing device 985 and one or more servers 988. The network 990 may be a wide-area network, such as the Internet, a local-area network, a metropolitan-area network, or another type of electronic communication network. The network 990 may include wired and/or wireless data links. A variety of communications protocols may be used in the network 990 including, but not limited to, Wi-Fi, Ethernet, Transport Control Protocol (TCP), Internet Protocol (IP), Hypertext Transfer Protocol (HTTP), SOAP, remote procedure call protocols, and/or other types of communications protocols.

In some examples, the additional computing device 988 is a dedicated web server as described above. In this example, the external computing device 985 can use an internet browser to communicate with the web server 988 to request and retrieve data. The data is then displayed to the user 905, such as by using a browser application. In some embodiments, the additional computing device 988 can be a cloud server configured to store in memory instructions for implementing the various operations, methods and functions disclosed herein. In such embodiments, the external computing device 985 may communicate with the computing device 988 to provide and/or receive data, instructions, etc., via, for example, the network 990. In some embodiments, the various operations, methods, and functions disclosed herein are implemented by instructions stored in memory. When the instructions are executed by the processor 908 of the one or more computing devices 985 or 988, the instructions cause the processor 908 to perform one or more of the operations or methods disclosed herein.

In some embodiments of the utilization scheme, the user 905 of the water bottle 100 can use an external computing device 985 for communicating with and for managing the utilization of the water bottle 100 via an application installed and executing on the portable computing device 985; some exemplary features of a mobile application that can be used for such purposes are presented below with reference to FIGS. 10A-10C. In some embodiments, data from the water bottle 100 (e.g., data collected from sensors onboard the water bottle 100) may be transferred to the portable computing device 985 via a network 990. In some embodiments, the network 990 may be bidirectional, i.e., the network may also be used by the portable computing device 985 to transmit data, instructions, etc., to the water bottle 100. For example, input data from the user 905 and/or data/instructions generated by the portable computing device 985 may be transmitted to the water bottle 100 for use in calculating, regulating, informing, etc., hydration level of the user 905. In some embodiments, the communication between the water bottle 100 and the portable computing device 985 may be routed via a network 990 to a cloud server or a web server.

In some embodiments, the portable computing device 985 may communicate with another computing device 988 via a network 990. The computing device 988 may be a server capable of processing the data transmitted to and from the portable computing device 985 (and/or, optionally, from the water bottle 100). For example, the computing device 988 may be a cloud server hosting computing devices with memory and processors to store and process, respectively, the received data to generate additional data/instructions for use in maintaining and determining hydration level of the user 905. It can also be configured to communicate with a weather server 992 that provides weather information for computing a target hydration level. In some embodiments, the computing device 988 can be configured as a standalone web server to receive, retrieve, process and/or generate data for similar purposes.

In some embodiments, the portable computing device 985 may communicate with another computing device 920 via a network 990. The computing device 920 may be a portable computing device 920 which may be access by another person 925, such as a coach, a fitness trainer, a healthcare professional or insurance personnel or anyone who would utilize the hydration data or to interact with the user's wellbeing. The computing device 920 can be any computing devices with memory and processors to store and process, respectively, the received data to generate additional data/ instructions for use in working with, maintaining and determining the hydration level of the user 905. It can also be used to directly communicate with the external computing device 985. It can also be configured to communicate with a weather server 992 that provides weather information for computing a target hydration level.

Using the Smart Water Bottle to Track Water Consumption

Figure 10A:
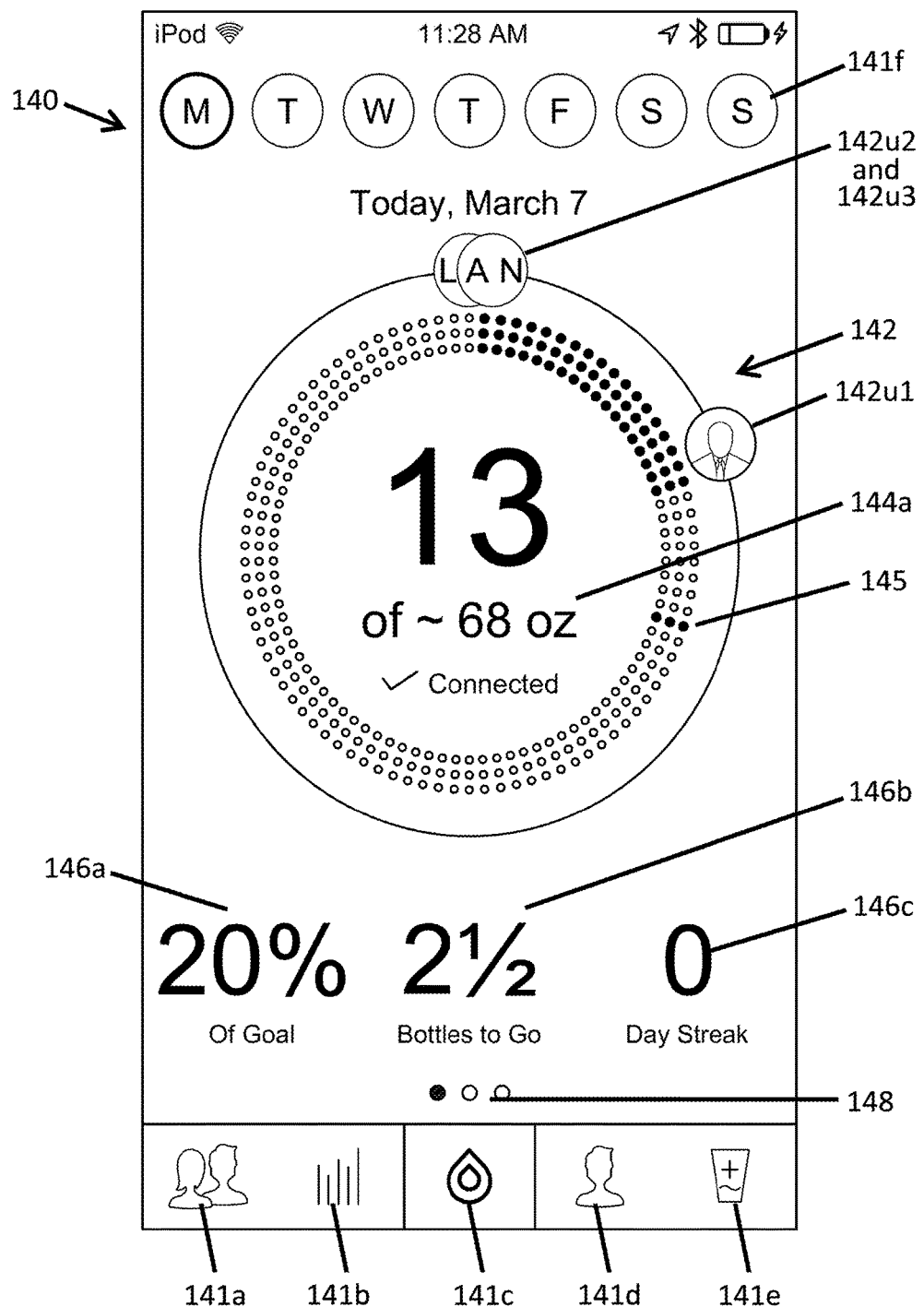
FIGS. 10A-10C illustrate a software interface on the portable computing device that interfaces with a smart water bottle.
Figure 10B:
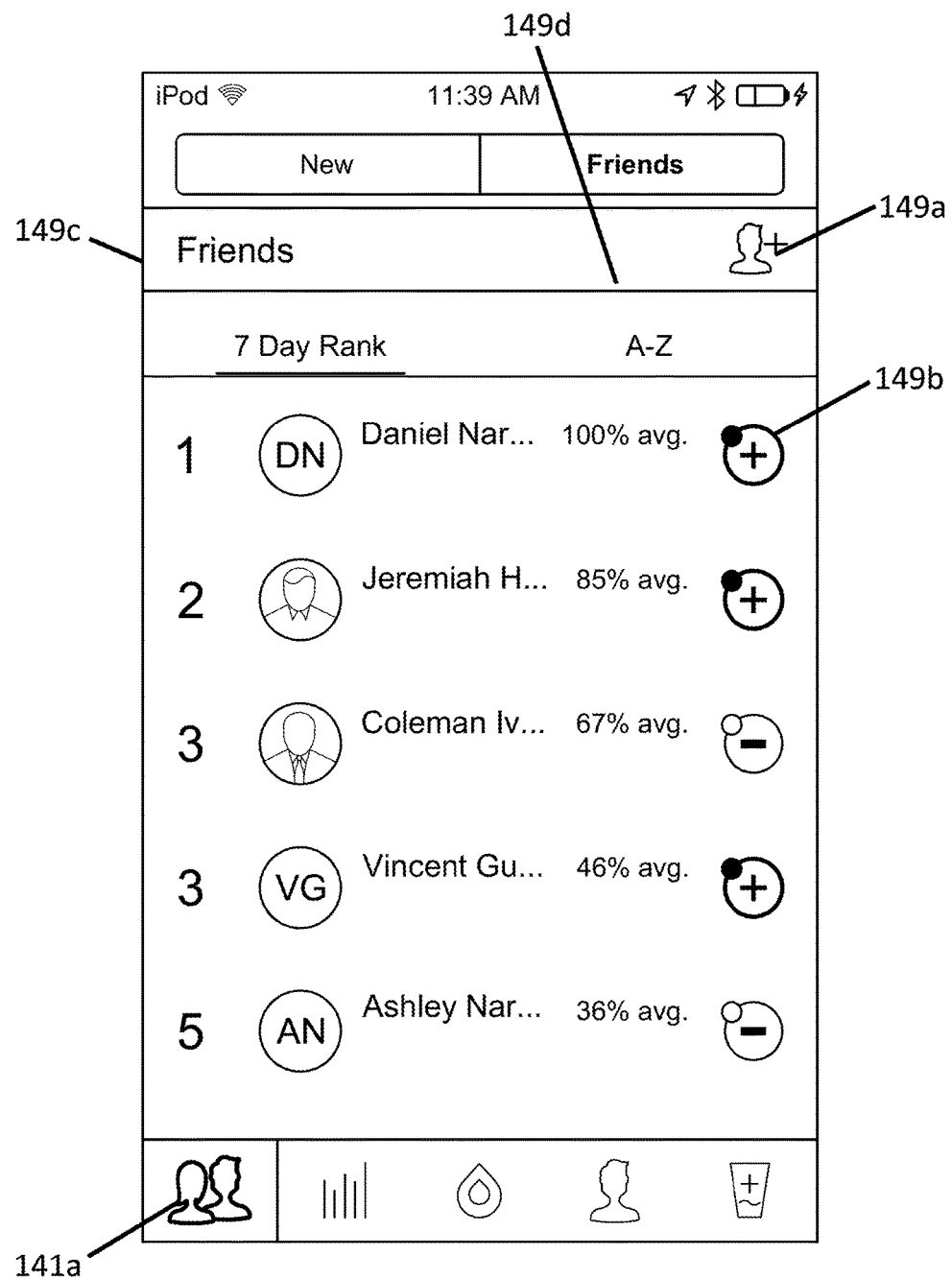
Figure 10C:
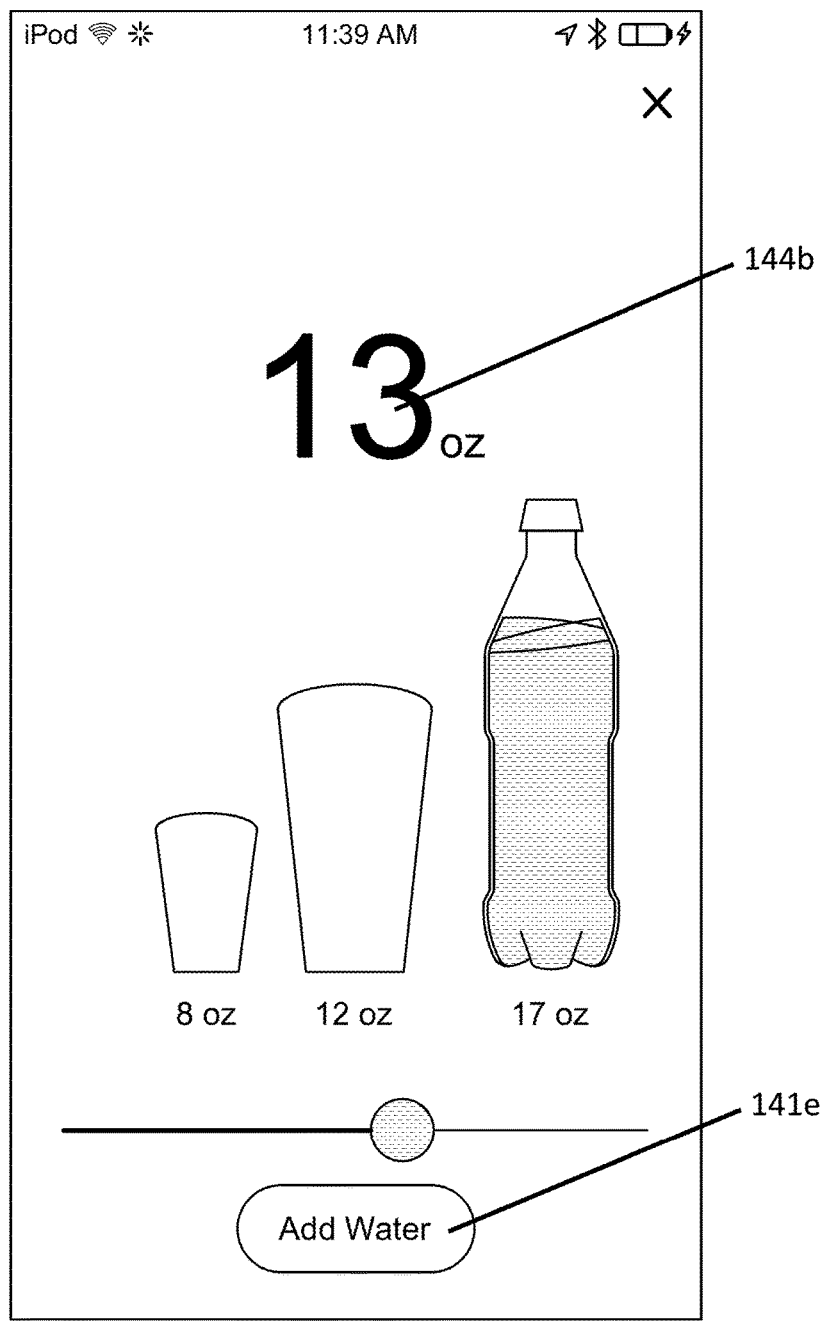

FIGS. 10A-10C illustrate a graphical user interface (GUI) 140 for the portable computing device 985. As shown in FIG. 10A, the GUI 140 includes several different tabs. Tab 141*a* links to "friends" and their water usage consumption, tab 141*b* links to the user's usage levels, tab 141*c* links to current progress (as displayed in FIG. 10A), tab 141*d* links to information about the owner, and tab 141*e* links to a notification page that allows the user to change his or her water consumption goal (e.g., for the user to add water manually). The GUI 140 also displays progress over the course of a week as indicated by day icons 141*f* The screen as shown in FIG. 10A is the primary screen to show the hydration progress. The GUI 140 also has additional pages as shown by the 3 dots indicating pages 148 near the bottom of the GUI. By swiping left to right or right to left, the pages 148 can show different aspects of the GUI 140.

FIG. 10A shows the GUI 140 display for tab 141*c*. In this tab, the GUI 140 shows a dynamic progress level graphic 142 that represents the amount of liquid consumed over a time period as a percentage of the recommended amount over that time period for different users. The circles with photos and initials 142*u*1, 142*u*2, and 142*u*3 represent the relative progress of the user and his or her "friends" towards their daily goals. Within the progress level graphic 142, the consumed level 144*a* is shown out of the recommended target level. For example, the current progress level of the user is 13 of 68 oz. consumed. The progress level graphic 142 also shows a target consumption level 145 based on the time of day and total consumption level.

The recommended target amount is calculated from various data about the user, including but not limited to: the user's physiology, including age, height, weight, and gender; the user's activity level; the user's global location and the ambient temperature and humidity at that location. The user's global location can be determined using the external device's GPS location data and data from the weather server. In an embodiment, the location information is used in conjunction with a Weather API to determine the real-time, current ambient temperature and humidity at that location. In an embodiment, the third source of data could be approximated by coupling the system with a weather prediction system or application for a period such that the liquid consumption requirements for the period could be estimated. In this embodiment liquid consumption requirements could be dynamic adjusting as the user moves locations or as the weather predictions become concrete measurements.

Another feature of the GUI 140 is a level status 146*a*, 146*b* and 146*c* of the amount of liquid that the user is recommended to consume, in this case expressed in terms of the complete volume of the container 100. For example, the status 146*a* shows the current level of progress as the percentage of the goal. The status 146*b* shows the amount of liquid recommended to consume in terms of bottles of water. The status 146*c* shows the consecutive days the user has maintained a desired hydration level.

FIG. 10B shows the GUI 140 under tab 141*a*. Here, the GUI 140 shows information about several of the user's "friends" who are in a network for sharing hydration data. Friends can be added using add button 149*a* and added friends can be removed by using remove button 149*b*. The hydration level or the accomplishments over a certain period of the user's friends can be ranked by pressing a "7-Day Rank" button 149*c* to show the relative progress of the people in the network. Otherwise, the hydration level of the user's friends can be shown alphabetically by pressing an "A-Z" button 149*d* to show the relative progress of all the people in the network.

FIG. 10C shows the "Add Water" screen available under tab 141*c*. The GUI 140 shows and allows the user to add a variable amount of water towards the user's daily tracked progress. In some embodiments, the GUI 140 may allow updating the user's recorded liquid intake, in case the user drinks liquid from sources other than the container 100, and which, therefore, cannot be directly recorded. Here, the indicator 144*b* shows the added amount of liquid as 13 oz.

Using the Smart Water Bottle to Track Water Consumption

A method or a process of using the smart water bottle is described as follows. In this exemplary process, the first step is to install the mobile application (depicted in FIGS. 10A-10C) on the user's mobile device 985, such as the user's smartphone. Once the application is installed, the user can then connect the application on the smartphone 985 to the smart water bottle 100. The user can then input appropriate parameters for the user, including the user's height, weight, medical information (e.g., medical history, allergies, and current medications), etc., so that the application can provide an estimated hydration goal. The user can also be provided with options to set his or her own hydration goal or to accept a recommended hydration goal based on his or her physiological data, activity level, and location.

The user can also set his or her notification preferences for meeting (or failing to meet) the hydration goal, e.g., by selecting or setting indications comprising illumination of the visual indicators 154 in a particular color, pulsation pattern, blinking rate, etc., or by creating distinct audible beeps or a vibration pattern to be delivered via the app 140/smart phone 985. Once the settings have been verified, the user can start filling the smart bottle with water and begin drinking as he or she normally would.

If the user is on target within the estimated hydration goal, the smart water bottle 100 may let the user know that he or she is on target by displaying a visual indication 1 (e.g., a particular pattern of flashes from the visual indicators 154). Alternatively, the smart bottle can also be set up in a way that if the user is on target with his or her hydration plan, no indication is set to display, or no alert is delivered to the user. If the user is lagging behind his or her hydration program, another indicator (e.g., indication 2, with a different pattern of output(s) from the visual indicator 154) can be used to notify the user. If the user is too far behind his or her hydration program, a third type of indication can be displayed to notify the user that he or she is too far behind her hydration level and that he or she should catch up in a more urgent fashion. This type of indicator can be indication 3, which can be similar to any notification types or forms as described for indication 2, but with more intensity. For example, the third type of indication can be blinking LEDs with higher frequency than those of indication 2 or audible beeps that are louder than those of indication 2. In some embodiments, the third type of indication can also be distinct from those notification LEDs, audible beeps or vibrations of indication 2. When water is fully consumed from the water bottle, a distinct notification can be used to notify the user to refill the bottle with water.

As use progresses, the smart water bottle 100 may transfer some or all of the collected hydration data to the smartphone application. The transfer can take place at any time of the day, but the user can set up a specific time or specific times at which the transfer to take place. For example, the user can set up to transfer hydration data at night when the hydration activities have been reduced so the transfer activities do not interfere with the various hydration measurements, such as liquid level measurements, or when the cap is opened, etc. The smart water bottle 100 may also transfer data automatically whenever the smart phone is within a given range and/or whenever queried by the smart phone.

Once the hydration data has been transferred to the application on the user's smartphone, the hydration data can be shared with other application or other users, including, for example, a fitness coach or healthcare professional, or on social media, such as via Facebook or Twitter. One of the benefits that the user can achieve by sharing hydration data is that the user can receive feedback via the app 140 on his or her hydration regime, which may help him or her with adjusting or modifying his or her goals based on those feedbacks. For example, a sports coach may monitor the data from an entire team, or a nurse may monitor the data of patients in their care.

The hydration data sharing can also benefit the community of fellow participants by building a database of hydration activities for everyone who participates or anyone with potential interest. The database can benefit any user who participates by providing complex hydration activities based on location of users, weather patterns, or the individual participant's activity level. In some embodiments, the user can be ranked according to the user's hydration level amongst the participants. The rankings of participants can be published in the database and/or displayed with the app 140. The rankings can serve as an incentive for the users to reach their hydration goals. In some embodiments, the users may be able to communicate with other users via the app 140 or social media so as to encourage or to motivate fellow participants, or perhaps to create a fun or competitive atmosphere.

Using the data input and/or gathered, in some embodiments, the processor and/or the external device may establish tailored recommended fluid consumption goals for the user. As the input information can be time dependent, the recommended goals can also be dynamic. The fluid consumption goals may include amount of fluid to be consumed, the rate of consumption, types of fluid to be consumed (e.g., nutrient levels, fluid temperature, etc.), and/or the like. In some embodiments, the processor and/or the external device, based on measurements taken by the various aforementioned sensors on the fluid container assembly, may evaluate whether the fluid inside the base container is configured to meet the recommended goals, and notify the user of the results of the evaluation. Further, after the recommended amount of time for the fluid consumption has passed and/or at a time chosen by the user, the processor and/or the external server may compare the recommended goals to the user's accomplishments.

Conclusion

Conventional terms in the fields of computer networking and computer systems have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Although specific embodiments have been illustrated and described herein, it will be appreciated by those of ordinary skill in the art that any arrangement that is calculated to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a machine-readable medium or machine-readable medium encoded with instructions operable to configure an electronic device to perform methods as described in the above examples. An implementation of such methods may include code, such as microcode, assembly language code, a higher-level language code, or the like. Such code may include machine-readable instructions for performing various methods. The code may form portions of computer program products. Further, in an example, the code may be tangibly stored on one or more volatile, non-transitory, or non-volatile tangible machine-readable media, such as during execution or at other times. Examples of these tangible machine-readable media may include, but are not limited to, hard disks, removable magnetic disks, removable optical disks (e.g., compact disks and digital video disks), magnetic cassettes, memory cards or sticks, random access memories (RAMs), read-only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure and is submitted with the understanding that it will not be used to interpret or limit the scope or meaning of the claims.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The invention claimed is:

1. A container assembly comprising:
   a container defining a cavity to hold a liquid;
   a liquid level sensor, disposed in the cavity, to measure a level of the liquid in the cavity;
   a processor, operably coupled to the liquid level sensor, to poll the liquid level sensor for a measurement of the level of the liquid in the cavity and to estimate a change in the level of the liquid in the cavity based on the measurement of the level of the liquid in the cavity;
   a visual indicator, operably coupled to the processor and disposed within the cavity, to provide a visual indication prompting a user to drink from the container; and
   an antenna, operably coupled to the processor, to transmit an indication of the change in the level of the liquid in the cavity to a wireless device.

2. The container assembly of claim 1, further comprising:
   an accelerometer, mechanically coupled to the container and operably coupled to the processor, to intermittently measure an acceleration of the container.

3. The container assembly of claim 2, wherein the processor is configured to poll the accelerometer intermittently and to poll the liquid level sensor if data from the accelerometer indicates that the container is vertically oriented.

4. The container assembly of claim 2, wherein the processor is configured to estimate the change in the level of the liquid in the cavity based on data from the accelerometer.

5. The container assembly of claim 1, wherein the processor is configured to cause the visual indicator to provide the visual indication in response to a command received from the wireless device via the antenna.

6. The container assembly of claim 5, wherein the command received from the wireless device via the antenna is based in part on a time since a last visual indication provided by the visual indicator.

7. The container assembly of claim 1, wherein:
   the antenna is configured to receive an indication of a target change in the level of the liquid in the cavity from the wireless device, and
   the processor is configured to compare the change in the level of the liquid in the cavity to the target change in the level of the liquid in the cavity and to cause the visual indicator to provide the visual indication if the change in the level of the liquid in the cavity is less than the target change in the level of the liquid in the cavity.

8. The container assembly of claim 7, wherein the target change in the level of the liquid in the cavity is based on at least one of an age of a user, a height of the user, a weight of the user, an activity level of the user, a location of the user, an ambient temperature, and an ambient humidity.

9. The container assembly of claim 1, wherein the visual indicator comprises at least one light-emitting diode (LED) disposed along a substrate extending into the cavity.

10. The container assembly of claim 9, wherein the at least one LED is configured to provide the visual indication by emitting light on a periodic basis.

11. The container assembly of claim 1, further comprising:
    a cap to keep the liquid within the cavity; and
    a cap sensor, operably coupled to the processor, to sense if the cap is coupled to the container,
    wherein the processor is configured to poll the liquid level sensor if the cap sensor indicates that the cap is coupled to the container.

12. The container assembly of claim 1, wherein the antenna is further configured to transmit an indication of when the visual indicator last provided the visual indication and to receive a command based on at least one of when the visual indicator last provided the visual indication, a target change in the level of the liquid in the cavity, or a predetermined period, the command causing the visual indicator to provide another visual indication prompting the user to drink from the container.

13. The container assembly of claim 1, wherein the liquid level sensor is configured to measure the level of the liquid in the cavity at intervals based on at least one of a time of day, a schedule of a user, or a power level of a power supply for the liquid level sensor.

14. The container assembly of claim 1, wherein the processor is configured to estimate a target liquid consumption rate for the user based on the measurement of the level of the liquid in the cavity and the visual indicator is configured to provide a visual indication based on the target consumption rate for the user.

15. The container assembly of claim 1, wherein the antenna is configured to receive a signal indicating a geographic position of the container assembly and the processor is configured to estimate a target consumption rate based on the geographic position of the container assembly.

16. A method of tracking consumption, by a user, of a liquid disposed within a container, the method comprising:
    (A) measuring, with an accelerometer mechanically coupled to the container, an acceleration of the container;
    (B) estimating, with a processor operably coupled to the accelerometer, an orientation of the container based on the acceleration;
    (C) determining if the orientation is within a predefined range of orientations;
    (D) in response to determining that the orientation is within the predefined range of orientations, measuring, with a liquid level sensor operably coupled to the processor, a level of the liquid in the container;
    (E) estimating a change in the level of the liquid in the cavity based on the level of the liquid in the cavity;
    (F) transmitting, via an antenna operably coupled to the processor, an indication of the change in the level of the liquid in the container to a wireless device; and
    (G) emitting light from a light source operably coupled to the processor and disposed in the container, the light prompting the user to drink at least some of the liquid in the container.

17. The method of claim 16, wherein:
    (C) comprises determining if the container is vertically oriented, and
    (D) comprises measuring the level of the liquid if the container is vertically oriented.

18. The method of claim 16, wherein estimating the change in the level of the liquid in (E) comprises estimating the change in the level of the liquid based the orientation of the container estimated in (B).

19. The method of claim 16, further comprising:
    performing steps (A) through (E) at periodic intervals.

20. The method of claim 16, further comprising:
sensing, with a cap sensor operably coupled to the processor, if a cap is coupled to the container, and
wherein (D) comprises measuring the level of the liquid if the cap sensor indicates that the cap is coupled to the container.

21. The method of claim 16, further comprising:
receiving, via the antenna, a command based on at least one of when the light source last emitted light; and
in response to the command, emitting additional light from to the light source disposed in the container, the additional light prompting the user to drink at least some of the liquid in the container.

22. The method of claim 16, wherein (G) comprises emitting the light at periodic intervals.

23. The method of claim 22, further comprising:
receiving a command, via the antenna, to emit light from the light source,
wherein the command is based on a comparison of the change estimated in (E) to a target change in the level of the liquid.

24. The method of claim 16, further comprising:
receiving, via the antenna, an indication of a target change in the level of the liquid, and
comparing, with the processor, the change in the level of the liquid in the cavity to the target change in the level of the liquid.

25. The method of claim 24, further comprising:
emitting the light from the light source in response to determining that the change in the level of the liquid is less than the target change in the level of the liquid.

26. The method of claim 24, wherein the target change in the level of the liquid in the cavity is based on at least one of an age of a user, a height of the user, a weight of the user, an activity level of the user, a location of the user, an ambient temperature, and an ambient humidity.

27. A container assembly comprising:
a translucent container to hold a liquid;
a substrate extending at least partway into the liquid;
a liquid level sensor, disposed on the substrate, to measure a level of the liquid;
an accelerometer, mechanically coupled to the translucent container, to measure an acceleration of the translucent container;
a processor, operably coupled to the accelerometer and the liquid level sensor, to (i) periodically determine an orientation of the translucent container based on acceleration measured by the accelerometer and (ii) periodically determine a change in the level of the liquid in the cavity based on the level of the liquid measured by the liquid level sensor and the orientation of the translucent container;
an antenna, operably coupled to the processor, to transmit the change in the level of the liquid to a wireless device; and
a light source, disposed on the substrate and operably coupled to the processor, to emit light (i) at periodic intervals and (ii) in response to a command received from the wireless device via the antenna,
wherein the command is based on (i) a comparison of the change in the level of the liquid and a desired change in the level of the liquid and (ii) a time since a last emission of light from the light source.

28. A fluid consumption monitoring system comprising:
a housing configured to couple with a beverage container;
a sensor coupled with said housing or that extends into said beverage container;
a wireless communication interface coupled with the housing;
a memory coupled with the housing; and
a processor coupled with the memory and the wireless communication interface and situated in the housing and configured to:
receive sensor data from the sensor;
calculate at least one of an amount of fluid inside of, dispensed from, and/or added to the beverage container from the sensor data;
store a representation of the amount of fluid in said memory; and
transmit the representation to an external device via the wireless communication interface when a wireless communication channel is available to the external device, the external device displaying the representation of the amount of fluid and a recommended amount of fluid for consumption by a user, the recommended amount based on an age, weight, and height of the user.

* * * * *